United States Patent
Rizk

(10) Patent No.: US 12,431,218 B2
(45) Date of Patent: Sep. 30, 2025

(54) MULTI-PASS SOFTWARE-ACCELERATED GENOMIC READ MAPPING ENGINE

(71) Applicant: Illumina, Inc., San Diego, CA (US)

(72) Inventor: Guillaume Alexandre Pascal Rizk, Rennes (FR)

(73) Assignee: Illumina, Inc., San Diego, CA (US)

( * ) Notice: Subject to any disclaimer, the term of this patent is extended or adjusted under 35 U.S.C. 154(b) by 56 days.

(21) Appl. No.: 18/117,088

(22) Filed: Mar. 3, 2023

(65) Prior Publication Data

US 2023/0290443 A1 Sep. 14, 2023

Related U.S. Application Data

(60) Provisional application No. 63/317,859, filed on Mar. 8, 2022.

(51) Int. Cl.
| | | |
|---|---|---|
| *G16B 30/10* | (2019.01) | |
| *G16B 20/00* | (2019.01) | |
| *G16B 20/20* | (2019.01) | |
| *G16B 30/00* | (2019.01) | |
| *G16B 40/20* | (2019.01) | |

(52) U.S. Cl.
CPC ............. *G16B 30/10* (2019.02); *G16B 20/00* (2019.02); *G16B 20/20* (2019.02); *G16B 30/00* (2019.02); *G16B 40/20* (2019.02)

(58) Field of Classification Search
CPC ........ G16B 30/10; G16B 20/20; G16B 20/00; G16B 40/20; G16B 30/00
See application file for complete search history.

(56) References Cited

U.S. PATENT DOCUMENTS

| | | |
|---|---|---|
| 5,859,972 A | 1/1999 | Subramaniam et al. |
| 5,964,072 A | 10/1999 | Rasmussen |
| 5,964,860 A | 10/1999 | Peterson et al. |
| 6,112,288 A | 8/2000 | Ullner |
| 6,253,529 B1 | 7/2001 | De Boer |
| 6,681,186 B1 | 1/2004 | Denisov et al. |
| 7,135,701 B2 | 11/2006 | Amin et al. |
| 7,533,068 B2 | 5/2009 | Maassen van den Brink et al. |
| 7,680,790 B2 | 3/2010 | Indeck et al. |
| 7,917,299 B2 | 3/2011 | Buhler et al. |
| 7,917,302 B2 | 3/2011 | Rognes |
| 7,945,668 B1 | 5/2011 | Nucci et al. |
| 7,948,015 B2 | 5/2011 | Rothberg et al. |
| 7,969,805 B2 | 6/2011 | Thom et al. |
| 8,190,548 B2 | 5/2012 | Choi |
| 8,195,596 B2 | 6/2012 | Rose et al. |
| 8,209,130 B1 | 6/2012 | Kennedy et al. |
| 8,217,433 B1 | 7/2012 | Fife |
| 8,280,640 B2 | 10/2012 | Levin et al. |
| 8,445,945 B2 | 5/2013 | Rothberg et al. |
| 8,524,487 B2 | 9/2013 | Fife |
| 8,558,288 B2 | 10/2013 | Rothberg et al. |
| 8,560,282 B2 | 10/2013 | Macready et al. |
| 8,594,951 B2 | 11/2013 | Homer |
| 8,620,923 B1 | 12/2013 | Wormley et al. |
| 8,700,689 B2 | 4/2014 | Macready et al. |
| 8,738,105 B2 | 5/2014 | Berkley et al. |
| 8,751,166 B2 | 6/2014 | Friedlander et al. |
| 8,798,936 B2 | 8/2014 | Bauer et al. |
| 8,847,799 B1 | 9/2014 | Kennedy et al. |
| 8,936,763 B2 | 1/2015 | Rothberg et al. |
| 9,014,989 B2 | 4/2015 | McMillen et al. |
| 9,026,574 B2 | 5/2015 | Macready et al. |
| 9,235,680 B2 | 1/2016 | Rooyen et al. |
| 9,322,872 B2 | 4/2016 | Hill |
| 9,355,365 B2 | 5/2016 | Berkley et al. |
| 9,405,876 B2 | 8/2016 | Macready et al. |
| 9,483,610 B2 | 11/2016 | McMillen et al. |
| 9,576,103 B2 | 2/2017 | McMillen et al. |

(Continued)

FOREIGN PATENT DOCUMENTS

| | | |
|---|---|---|
| AU | 2014335877 A1 | 5/2016 |
| CN | 102308206 A | 1/2012 |

(Continued)

OTHER PUBLICATIONS

Roy et al., Turtle: Identifying frequent k-mers with cache-efficient algorithms, 2014, Bioinformatics, 30(14), p. 1950-1957 (Year: 2014).*

Ahmed et al., A Comparison of Seed-and-Extend Techniques in Modern DNA Read Alignment Algorithms, 2016, BIBM, p. 1421-1428 (Year: 2016).*

Kim et al., A review on Sequence Alignment Algorithms for Short Reads Based on Next-Generation Sequencing, 2020, IEEE, 8, p. 189811-189822 (Year: 2020).*

Alser et al., "Technology dictates algorithms: recent developments in read alignment," Genome Biology, Aug. 26, 2021, 22(1):249, 74 pages.

Langmead, "ADS1: Variations on k-mer indexes", Jun. 18, 2015, retrieved Jul. 13, 2023 from URL <https://www.youtube.com/watch?v=My_sw_Rf_4U>, 1 page.

(Continued)

*Primary Examiner* — Kaitlyn L Minchella
(74) *Attorney, Agent, or Firm* — Heslin Rothenberg Farley & Mesiti P.C.; Matthew M. Hulihan, Esq.

(57) ABSTRACT

Methods, systems, and apparatus, including computer programs encoded on computer-storage media, for software-accelerated genomic data read mapping are described. In some implementations, software-accelerated genomic data read mapping includes obtaining a first k-mer seed from a genomic data read; generating a genomic signature based on a first k-mer seed; determining a reference sequence location using a hash data structure based on the genomic signature; determining a number of mismatches; based on determining the number of mismatches includes one or more mismatches, obtaining, by the one or more computers, a set of k-mer seeds from the genomic data read; and based on the set of k-mer seeds from the genomic data read, selecting, by the one or more computers, an actual alignment for the genomic data read.

20 Claims, 6 Drawing Sheets

(56) References Cited

U.S. PATENT DOCUMENTS

| | | |
|---|---|---|
| 9,618,474 B2 | 4/2017 | van Rooyen et al. |
| 9,679,104 B2 | 6/2017 | van Rooyen et al. |
| 9,792,405 B2 | 10/2017 | van Rooyen et al. |
| 10,049,179 B2 | 8/2018 | van Rooyen et al. |
| 10,068,052 B2 | 9/2018 | van Rooyen et al. |
| 10,068,183 B1 | 9/2018 | van Rooyen |
| 10,090,857 B2 | 10/2018 | Bhola et al. |
| 10,179,937 B2 | 1/2019 | Babiarz et al. |
| 11,049,588 B2 | 6/2021 | van Rooyen et al. |
| 11,527,307 B2 | 12/2022 | Rizk et al. |
| 11,776,663 B2 | 10/2023 | Rizk et al. |
| 12,080,385 B2 | 9/2024 | Rizk et al. |
| 2003/0033279 A1 | 2/2003 | Gibson et al. |
| 2003/0033501 A1 | 2/2003 | Cooke et al. |
| 2003/0039362 A1 | 2/2003 | Califano et al. |
| 2003/0104470 A1 | 6/2003 | Fors et al. |
| 2004/0024536 A1 | 2/2004 | Rognes |
| 2004/0059721 A1 | 3/2004 | Patzer |
| 2004/0098203 A1 | 5/2004 | Rognes |
| 2004/0126840 A1 | 7/2004 | Cheng et al. |
| 2004/0142463 A1 | 7/2004 | Walker et al. |
| 2005/0060195 A1 | 3/2005 | Bessette et al. |
| 2005/0131649 A1 | 6/2005 | Larsen et al. |
| 2005/0228595 A1 | 10/2005 | Cooke et al. |
| 2006/0225165 A1 | 10/2006 | Maassen van den Brink et al. |
| 2007/0038381 A1 | 2/2007 | Melchior et al. |
| 2007/0078897 A1 | 4/2007 | Hayashi et al. |
| 2007/0088510 A1 | 4/2007 | Li et al. |
| 2007/0196816 A1 | 8/2007 | Schwartz et al. |
| 2008/0005024 A1 | 1/2008 | Kirkwood |
| 2008/0050782 A1 | 2/2008 | Selifonov et al. |
| 2008/0086274 A1 | 4/2008 | Chamberlain et al. |
| 2008/0176750 A1 | 7/2008 | Rose et al. |
| 2008/0250016 A1 | 10/2008 | Farrar |
| 2009/0121215 A1 | 5/2009 | Choi |
| 2009/0125248 A1 | 5/2009 | Shams et al. |
| 2009/0171647 A1 | 7/2009 | Mannava et al. |
| 2009/0253130 A1 | 10/2009 | Yoo |
| 2009/0270277 A1 | 10/2009 | Glick et al. |
| 2010/0077267 A1 | 3/2010 | Perego et al. |
| 2010/0082805 A1 | 4/2010 | Orton et al. |
| 2010/0085827 A1 | 4/2010 | Thom et al. |
| 2010/0169313 A1 | 7/2010 | Kenedy et al. |
| 2010/0281401 A1 | 11/2010 | Tebbs et al. |
| 2010/0327847 A1 | 12/2010 | Leiber et al. |
| 2011/0004413 A1 | 1/2011 | Carnevali et al. |
| 2011/0093581 A1 | 4/2011 | Ventatachalm |
| 2011/0184235 A1 | 7/2011 | Schostek et al. |
| 2011/0227043 A1 | 9/2011 | Guo et al. |
| 2011/0231446 A1 | 9/2011 | Buhler et al. |
| 2011/0288785 A1 | 11/2011 | Tembe |
| 2012/0001615 A1 | 1/2012 | Levine |
| 2012/0089339 A1 | 4/2012 | Ganeshalingam et al. |
| 2012/0102041 A1 | 4/2012 | Park et al. |
| 2012/0109849 A1 | 5/2012 | Chamberlain et al. |
| 2012/0135394 A1 | 5/2012 | Kim et al. |
| 2012/0149981 A1 | 6/2012 | Khait et al. |
| 2012/0214172 A1 | 8/2012 | Chen et al. |
| 2013/0018599 A1 | 1/2013 | Peng |
| 2013/0031092 A1 | 1/2013 | Bhola et al. |
| 2013/0091121 A1 | 4/2013 | Galinsky |
| 2013/0110407 A1 | 5/2013 | Baccash et al. |
| 2013/0124100 A1 | 5/2013 | Drmanac et al. |
| 2013/0144925 A1 | 6/2013 | Macready et al. |
| 2013/0157870 A1 | 6/2013 | Pushkarev et al. |
| 2013/0194882 A1 | 8/2013 | Ishii et al. |
| 2013/0204851 A1 | 8/2013 | Bhola et al. |
| 2013/0245958 A1 | 9/2013 | Forster et al. |
| 2013/0254202 A1 | 9/2013 | Friedlander et al. |
| 2013/0275486 A1 | 10/2013 | Dickinson et al. |
| 2013/0296175 A1 | 11/2013 | Rafnar et al. |
| 2013/0297221 A1 | 11/2013 | Johnson et al. |
| 2013/0307029 A1 | 11/2013 | Xu et al. |
| 2013/0311106 A1 | 11/2013 | White et al. |
| 2013/0316331 A1 | 11/2013 | Isakov et al. |
| 2013/0324417 A1 | 12/2013 | Kennedy et al. |
| 2013/0332081 A1 | 12/2013 | Reese et al. |
| 2013/0338012 A1 | 12/2013 | Sulem et al. |
| 2013/0338934 A1 | 12/2013 | Asadi et al. |
| 2014/0024537 A1 | 1/2014 | Rigatti et al. |
| 2014/0025312 A1 | 1/2014 | Chin et al. |
| 2014/0033125 A1 | 1/2014 | Merel |
| 2014/0045705 A1 | 2/2014 | Bustamante et al. |
| 2014/0046926 A1 | 2/2014 | Walton |
| 2014/0051588 A9 | 2/2014 | Drmanac et al. |
| 2014/0081665 A1 | 3/2014 | Holmes |
| 2014/0114582 A1 | 4/2014 | Mittelman et al. |
| 2014/0121116 A1 | 5/2014 | Richards et al. |
| 2014/0164516 A1 | 6/2014 | Maltbie et al. |
| 2014/0200166 A1 | 7/2014 | Van Rooyen et al. |
| 2014/0236490 A1 | 8/2014 | Van Rooyen et al. |
| 2014/0297196 A1 | 10/2014 | Olson |
| 2014/0304276 A1 | 10/2014 | Boyce |
| 2014/0309944 A1 | 10/2014 | van Rooyen et al. |
| 2014/0310215 A1 | 10/2014 | Trakadis |
| 2014/0316716 A1 | 10/2014 | Jiang et al. |
| 2014/0337052 A1 | 11/2014 | Pellini et al. |
| 2014/0350968 A1 | 11/2014 | Hahn et al. |
| 2014/0361911 A1 | 12/2014 | Kennedy et al. |
| 2014/0368550 A1 | 12/2014 | Vaske et al. |
| 2014/0371109 A1 | 12/2014 | McMillen et al. |
| 2014/0371110 A1* | 12/2014 | Van Rooyen ..... H01L 21/76886 438/618 |
| 2015/0066824 A1 | 3/2015 | Harris et al. |
| 2015/0123600 A1 | 5/2015 | Groat et al. |
| 2015/0142334 A1 | 5/2015 | Mishra |
| 2015/0149510 A1 | 5/2015 | Kennedy et al. |
| 2015/0154406 A1 | 6/2015 | Nachrig et al. |
| 2015/0211055 A1 | 7/2015 | Apte et al. |
| 2015/0227686 A1 | 8/2015 | Sheinin et al. |
| 2015/0227697 A1 | 8/2015 | Nelson et al. |
| 2015/0248525 A1 | 9/2015 | Ury et al. |
| 2015/0286495 A1 | 10/2015 | Lee |
| 2015/0310163 A1 | 10/2015 | Kingsmore et al. |
| 2015/0339437 A1 | 11/2015 | McMillen et al. |
| 2015/0363550 A1 | 12/2015 | Green, Jr. et al. |
| 2016/0046986 A1 | 2/2016 | Eltoukhy et al. |
| 2016/0057246 A1 | 2/2016 | Krishnaiahsetty |
| 2016/0092631 A1 | 3/2016 | Yandell et al. |
| 2016/0140290 A1 | 5/2016 | Rooyen et al. |
| 2016/0154795 A1 | 6/2016 | Kennedy et al. |
| 2016/0171153 A1 | 6/2016 | Van Rooyen et al. |
| 2016/0178569 A1 | 6/2016 | Hoffman et al. |
| 2016/0188793 A1 | 6/2016 | Muzzey et al. |
| 2016/0283407 A1 | 9/2016 | Van Rooyen et al. |
| 2016/0306923 A1 | 10/2016 | van Rooyen et al. |
| 2017/0068776 A1 | 3/2017 | Godinez-Moreno et al. |
| 2017/0107576 A1 | 4/2017 | Babiarz et al. |
| 2017/0116216 A1 | 4/2017 | Kennedy et al. |
| 2017/0124254 A1 | 5/2017 | Rooyen et al. |
| 2017/0237445 A1 | 8/2017 | Cox et al. |
| 2017/0270245 A1 | 9/2017 | van Rooyen et al. |
| 2017/0308644 A1 | 10/2017 | van Rooyen et al. |
| 2017/0357665 A1 | 12/2017 | Olivares-Amaya et al. |
| 2018/0121601 A1 | 5/2018 | Hahm et al. |
| 2018/0152535 A1 | 5/2018 | Sade et al. |
| 2018/0189444 A1 | 7/2018 | van Rooyen et al. |
| 2018/0196916 A1 | 7/2018 | van Rooyen et al. |
| 2018/0196917 A1 | 7/2018 | van Rooyen et al. |
| 2018/0239865 A1 | 8/2018 | van Rooyen et al. |
| 2018/0240032 A1 | 8/2018 | van Rooyen |
| 2019/0130998 A1 | 5/2019 | van Rooyen et al. |
| 2019/0171963 A1 | 6/2019 | van Rooyen |
| 2019/0172558 A1 | 6/2019 | van Rooyen et al. |
| 2019/0214111 A1 | 7/2019 | Alberti et al. |
| 2019/0385702 A1 | 12/2019 | Alberti et al. |
| 2021/0074381 A1 | 3/2021 | Rizk et al. |
| 2021/0193261 A1 | 6/2021 | Van Rooyen et al. |
| 2021/0257052 A1 | 8/2021 | Van Rooyen et al. |
| 2021/0313014 A1 | 10/2021 | van Rooyen |
| 2022/0139502 A1 | 5/2022 | Rizk et al. |
| 2022/0415441 A1 | 12/2022 | Rizk et al. |
| 2023/0040143 A1 | 2/2023 | Rizk et al. |
| 2024/0062853 A1 | 2/2024 | Rizk et al. |

(56) References Cited

U.S. PATENT DOCUMENTS

| | | |
|---|---|---|
| 2024/0194296 A1 | 6/2024 | Rizk |
| 2024/0395359 A1 | 11/2024 | Onuchic et al. |
| 2024/0395363 A1 | 11/2024 | Han et al. |
| 2024/0420804 A1 | 12/2024 | Rizk et al. |
| 2025/0046399 A1 | 2/2025 | Rizk et al. |

FOREIGN PATENT DOCUMENTS

| | | |
|---|---|---|
| CN | 102521528 A | 6/2012 |
| CN | 103293209 A | 9/2013 |
| CN | 103336916 A | 10/2013 |
| CN | 104428425 A | 3/2015 |
| CN | 107851137 A | 3/2018 |
| CN | 105051741 B | 4/2018 |
| CN | 110168649 A | 8/2019 |
| EP | 2313523 A2 | 4/2011 |
| EP | 2759952 A1 | 7/2014 |
| EP | 3317440 A4 | 3/2019 |
| EP | 3465507 B1 | 9/2021 |
| JP | 2007-108949 A | 4/2007 |
| JP | 2016-514291 A | 5/2016 |
| JP | 2014-146318 A | 8/2021 |
| KR | 1020130088512 A | 8/2013 |
| RU | 2282242 C2 | 8/2006 |
| RU | 2015144109 A | 4/2017 |
| WO | WO 2006/110855 A2 | 10/2006 |
| WO | WO 2011/149534 A2 | 12/2011 |
| WO | WO 2012/122546 A2 | 9/2012 |
| WO | WO 2013/128371 A2 | 9/2013 |
| WO | WO 2014/060305 A1 | 4/2014 |
| WO | WO 2014/074246 A1 | 5/2014 |
| WO | WO 2014/113736 A1 | 7/2014 |
| WO | WO 2014/121091 A1 | 8/2014 |
| WO | WO 2014/186604 A1 | 11/2014 |
| WO | WO 2015/051006 A2 | 4/2015 |
| WO | WO 2015/089333 A1 | 6/2015 |
| WO | WO 2015/100427 A1 | 7/2015 |
| WO | WO 2015/123600 A1 | 8/2015 |
| WO | WO 2015/166389 A1 | 11/2015 |
| WO | WO 2016/051429 A1 | 4/2016 |
| WO | WO 2016/061396 A1 | 4/2016 |
| WO | WO 2016/168371 A1 | 10/2016 |
| WO | WO 2017/004589 | 1/2017 |
| WO | WO 2018/068829 A1 | 4/2018 |
| WO | WO 2018/071054 A1 | 4/2018 |
| WO | WO 2018/071078 A1 | 4/2018 |
| WO | WO 2020/023882 A1 | 1/2020 |
| WO | WO 2002/086161 A1 | 10/2022 |

OTHER PUBLICATIONS

Li et al., "A survey of sequence alignment algorithms for next-generation sequencing," Briefings in Bioinformatics, Sep. 1, 2010, 11(5):473-83.
PCT International Search Report and Written Opinion in International Appln. No. PCT/US2023/063661, dated Jun. 6, 2023, 18 pages.
PCT International Preliminary Report on Patentability in International Appln. No. PCT/US2023/063661, mailed on Sep. 19, 2024, 11 pages.
[No Author], "Chap 5 Dictionary Techniques," Aug. 23, 2016, retrieved from URL <http://se.csie.dyu.edu.tw/lairrol/files/DC/chap5.pdf>, 55 pages.
[No Author], "History of Lossless Data Compression Algorithms," Jul. 28, 2014, retrieved from URL <http://ieeeghn.org/wiki/index.php?title=History_of_Lossless_Data_Co+A7mpression_Algorithms&oldid=96464&printable=yes&useskin=vector>, 16 pages.
Abbas et al., "Combining Executin Pipelines to Improve Parallel Implementation of HMMER on FPGA," Microprocessors and Microsystems, Jun. 2015, 39(7):457-470.
Akita.com, "Science of Akita, RNA Sequence Manuals" Dec. 18, 2014, retrieved Sep. 4, 2024 from URL <https://www.dbp.akita-pu.ac.jp/esuzuki/RNASeq_manuals/30ddbjing_Pipeline.pdf>, 2-55 (no translation available).
Al Junid et al., "Development of Novel Data Compression Technique for Accelerate DNA Sequence Alignment Based on Smith-Waterman Algorithm," Paper, Presented at the Third UKSim European Symposium on Computer Modeling and Simulation, Athens, Greece, Nov. 25-27, 2009; IEEE, Dec. 2009, pp. 181-186.
Al Junid et al., "Optimization of DNA Sequences Data for Accelerate DNA Sequences Alignment on FPGA," Paper, Presented at the 2010 Fourth Asia International Conference on Mathematical/Analytical Modelling and Computer Simulation, Kota Kinabalu, Malaysia, May 26-28, 2010; IEEE, Jun. 2010, pp. 231-236.
Al Tera Corp, "Implementation of the Smith-Waterman Algorithm on a Reconfigurable Supercomputing Platform," White Paper, Sep. 2007, version 1, 18 pages.
Alachiotis et al., "Accelerating Phylogeny-Aware Short DNA Read Alignment with FPGAs," The Exelixis Lab, Heidelberg Institute for Theoretical Studies, Heidelberg, Germany, 2011, 8 pages.
Angiuoli et al., "Mugsy: fast multiple alignment of closely related whole genomes," Bioinformatics, published online Dec. 9, 2010, published in print 2011, retrieved on May 25, 2016, retrieved from URL <http://bioinformatics.oxfordjournals.org/content/27/31334.full>, 27(3):334-342.
Anonymous: "FPGA-accelerated Bioinformics at #ASHG-Dragen Aligner from Edico Genome," Oct. 20, 2014, XP055360856, retrieved on Mar. 31, 2017, retrieved from URL <http://moolog.us/blogs/glob/2014/210/20/fpga-accelerated-bioinform ics-at-ashg-dragenaligner- from-edico-genome/#>, 7 pages.
AU Office Action in Australian Appln. No. 2017207317, dated Aug. 31, 2022, 6 pages.
AU Office Action in Australian Appln. No. 2017207317, mailed on Sep. 3, 2021, 6 pages.
AU Office Action in Australian Appln. No. 2022228089, mailed on Oct. 3, 2023, 5 pages.
AU Office Action in Australian Appln. No. 2022228089, mailed on Sep. 23, 2024, 3 pages.
AU Office Action in Australian Appln. No. 2022252718, mailed on Jul. 19, 2024, 3 pages.
AU Office Action in Australian Appln. No. 2022252718, mailed on Jul. 27, 2023, 3 pages.
Benkrid et al., "A highly parameterized and efficient FPGA-based skeleton for pairwise biological sequence alignment," IEEE Transactions on VLSI Systems, IEEE Educational Activities Dept. Piscataway, NJ, Apr. 2009, pp. 561-570 (1-12).
Benkrid et al., "High Performance Biological Pairwise Sequence Alignment: FPGA versus GPU versus Cell BE versus GPP," International Journal of Reconfigurable Computing, 2012, 2012:752910, 16 pages.
Benkrid et al., "A High Performance Reconfigurable Core for Motif Searching Using Profile HMM," Paper, Presented at the 2008 NASA/ESA Conference on Adaptive Hardware and Systems, Noordwijk, Netherlands, Jun. 22-25, 2008; IEEE, Aug. 2008, pp. 285-292.
Benoit et al., "NGS Data Compression," Algorithms for Next-Generation Sequencing Data, Dec. 2017, pp. 91-115.
Booth et al., "Bio-Linux as a tool for bioinformatics training," Paper, Presented at the 2012 IEEE 12th International Conference on Bioinformatics & Bioengineering (BIBE), Larnaca, Cyprus, Nov. 11-13, 2012; IEEE, Jan. 2013, pp. 578-582.
BR Office Action in Brazilian Appln. No. 1220230005996, mailed on Sep. 16, 2024, 11 pages (with English translation).
BR Office Action in Brazilian appln. No. BR112018014086-4, mailed on Sep. 16, 2022, 8 pages (with English translation).
Buyukkurt et al., "Compiler Generated Systolic Arrays for Wavefront Algorithm Acceleration on FPGAs," Paper, Presented at the 2008 International Conference on Field Programmable Logic and Applications, Heidelberg, Germany, Sep. 8-10, 2008; IEEE, Sep. 2008, 4 pages.
CA Office Action in Canadian Appln. No. 3,008,176, mailed on Feb. 21, 2023, 5 pages.
CA Office Action in Canadian Appln. No. 3,026,644, mailed on Jul. 21, 2023, 4 pages.

(56) References Cited

OTHER PUBLICATIONS

CA Office Action in Canadian Appln. No. 3,148,960, mailed on Dec. 14, 2023, 7 pages.
CA Office Action in Canadian Appln. No. 3,148,976, mailed on Jan. 5, 2024, 6 pages.
CA Office Action in Canadian Appln. No. 3,174,208, mailed on Apr. 11, 2024, 5 pages.
CA Office Action in Canadian Appln. No. 3026644, mailed on Apr. 10, 2024, 7 pages.
CA Office Action in Canadian Appln. No. 3148976, mailed on Oct. 15, 2024, 6 pages.
Cánovas et al., "Lossy compression of quality scores in genomic data," Bioinformatics, Aug. 2014, 30(15):2130-2136.
Carneiro, "Accelerating Variant Calling," Powerpoint Presentation, Broad Institute, Intel Genomic Sequencing Pipeline Workshop, Mount Sinai, New York, Dec. 10, 2013, 26 pages.
Chang et al., "Exploring Sequence Alignment Algorithms on FPGA-based Heterogeneous B Architectures," Paper, Presented at the International Work- Conference on Bioinformatics and Biomedical Engineering, Granada, Spain, Apr. 7-9, 2014, pp. 330-341.
Chang et al., "FPGA-based Heterogeneous Architecture for Sequence Alignment," The XIV Microelectronics, Students Forum, Sep. 2014, 4 pages.
Chang et al., "The SMEM Seeding Acceleration for DNA Sequence Alignment," Paper, Presented at the 2016 IEEE 24th Annual International Symposium on Field-Programmable Custom Computing Machines (FCCM), Washington D.C., USA, May 1-3, 2016; IEEE, Aug. 2016, pp. 32-39.
Choi et al., "A quantitative analysis on microarchitectures of modern CPU-FPGA platforms," Paper, Presented at the DAC '16: Proceedings of the 53rd Annual Design Automation Conference, Austin, Texas, Jun. 5-9, 2016, 6 pages.
Choi et al., "Impact of Cache Architectures and Interface on Performance and Area of FPGA-Based Processor/Parallel-Accelerator Systems," Paper, Presented at the 2012 IEEE 20th International Symposium on Field-Programmable Custom Computing Machines (FCCM), Toronto, Canada, Apr. 29 - May 1, 2012; IEEE, Jul. 2012, pp. 17-24.
Chrysanthou et al., "Parallel Accelerators for GlimmerHMM Bioinformatics Algorithm," Paper, Presented at the 2011 Design, Automation & Test in Europe, Grenoble, France, Mar. 14-18, 2011; IEEE, May 2011, 6 pages.
Chrysos et al., "Reconfiguring the Bioinformatics Computational Spectrum: Challenges and Opportunities of FPGA-Based Bioinformatics Acceleration Platforms," IEEE Design & Test, Oct. 2013, 31(1):62-73.
CN Office Action in Chinese Appln. No. 201780006359.1, mailed on Jul. 30, 2021, 37 pages (with English translation).
CN Office Action in Chinese Appln. No. 201780035840.3, mailed on Aug. 9, 2023, 4 pages (with English translation).
CN Office Action in Chinese Appln. No. 201780035840.3, mailed on Sep. 5, 2022, 12 pages (with English translation).
CN Office Action in Chinese Appln. No. 202080062727.6, mailed on Dec. 17, 2024, 16 pages (with English translation).
CN Office Action in Chinese Appln. No. 202210534739.5, mailed on Jul. 11, 2024, 17 pages (with English translation).
Derrien et al., "Fast Computation and Applications of Genome Mappability," PLOS One, Jan. 2012, retrieved on May 25, 2016, retrieved from URL <https://journals.plos.org/plosone/article?id=10.1371/journal.pone.0030377>, 15 pages.
Derrien et al., "Hardware acceleration of HIMMER on FPGAs," Journal of Signal Processing Systems, Jul. 2010, 58(1):53-67.
Deutsch, "Quantum theory, the Church-Turing principle and the universal quantum computer," Proceedings of the Royal Society of London A 400, 1985, pp. 97-117.
Dilthey et al., "Improved genome inference in the MHC using a population reference graph," Nature Genetics, Apr. 2015, 47:682-688.
Doddavula et al., "Implementation of a Scalable Next Generation Sequencing Business Cloud Platform—An Experience Report," Paper, Presented at the 2011 IEEE 4th International Conference on Cloud Computing, Washington D.C., USA, Jul. 4-9, 2011; IEEE, Sep. 2011, pp. 598-605.
Dydel et al., "Large Scale Protein Sequence Alignment Using FPGA Reprogrammable Logic Devices," Lecture Notes, Presented at the 4th International Conference of Field Programmable Logic and Application (FPL), Leuven, Belgium, Aug. 30-Sep. 1, 2004, 3203:23-32.
EP European Search Report in European Appln. No. 14740602.9, dated Mar. 15, 2022, 14 pages.
EP European Search Report in European Appln. No. 19199685.9, dated Jan. 3, 2020, 13 pages.
EP Extended European Search Report in European Appln. No. 23195421.5, mailed on Mar. 7, 2024, 12 pages.
EP Extended European Search Report in European Appln. No. 24162764.5, mailed on Jun. 17, 2024, 9 pages A43.
EP Extended Search Report in European Appln. No. 21179125.6, mailed on Nov. 29, 2021, 9 pages.
EP Office Action in European Appln. No. 17731690, mailed on Jan. 4, 2020, 19 pages.
EP Office Action in European Appln. No. 17731690.8, mailed on Apr. 1, 2020, 19 pages.
EP Office Action in European Appln. No. 20780856.9, mailed on Aug. 20, 2024, 10 pages.
EP Office Action in European Appln. No. 21179125.6, mailed on Dec. 10, 2024, 6 pages.
EP Office Action in European Appln. No. 21190670.6, mailed on Feb. 1, 2023, 8 pages.
Eusse et al., "A Protein Sequence Analysis Hardwar Accelerator Based on Divergences," International Journal of Reconfigurable Computing, Jan. 2012, 2012:2017378, 19 pages.
Faes et al., "Scalable Hardware Accelerator for Comparing DNA and Protein Sequences," Paper, Presented at the InfoScale '06: Proceedings of the 1st International Conference on Scalable Information Systems, Hong Kong, China, May 30-Jun. 1, 2006, 6 pages.
Fagin et al., "FPGA and Rapid Prototyping Technology Use in a Special Purpose Computer for Molecular Genetics," 1992, Thayer School of Engineering, retrieved on Jan. 11, 2017, retrieved from URL <http://www.faginfamily.net/barry/Papers/ICCD92.htm>, 6 pages.
Fernandez et al., "Exploration of Short Reads Genome Mapping in Hardwares," Paper, Prasented at the 20th International Conference on Field Programmable Logic and Applications (FPL), Milano, Italy, Aug. 31-Sep. 2, 2010, 4 pages.
Fernandez et al., "Multithreaded FPGA Acceleration of DNA Sequence Mapping," Paper, Presented at the 2012 IEEE Conference on High Performance Extreme Computing, Waltham, Massachusets, Sep. 10-12, 2012; IEEE, Jan. 2013, 6 pages.
Fernandez et al., "Multithreaded FPGA Acceleration of DNA Sequence Mapping," PowerPoint Presentation, UC Riverside, Department of Computer Science and Engineering Jacquard Computing, 2012, 20 pages.
Ferraz et al., "Evaluating Optimization Strategies for HMMer Acceleration on GPU," Paper, Presented at the 2013 International Conference on Parallel and Distributed Systems, Seoul, South Korea, Dec. 15-18, 2013; IEEE, May 2014, pp. 59-68.
Feynman, "Simulating Physics with Computers," International Journal of Theoretical Physics, 1982, 21(6/7):467-488.
Fromer et al., "Discovery and statistical genotyping of copy-number variation from whole-exome sequencing depth, " The American Journal of Human Genetics, Oct. 2012, 91(4):597-607.
Giraldo et al., "A Hmmer hardware accelerator using divergences, " Paper, Presented at the 2010 Design, Automation & Test in Europe Conference & Exhibition (DATE 2010), Dresden, Germany, Mar. 8-12, 2010; IEEE, Apr. 2010, pp. 405-410.
Github.com [online], "Spring," Jan. 24, 2020, retrieved on Jan. 16, 2025, retrieved from URL <https://github.com/shubhamchandak94/Spring >, 7 pages.
Grabherr et al., "Genome-wide synteny through highly sensitive sequence alignment: Satsuma, " Bioinformatics, May 2010, 26(9):1145-1151.
Grabowski et al., "Engineering Relative Compression of Genomes," CoRR, Submitted on Mar. 11, 2011, arXiv:1103.2351v1, 12 pages.

(56) References Cited

OTHER PUBLICATIONS

Guccione et al., "Gene Matching Using JBits," Paper, Presented at the 12th International Conference on Field Programmable Logic and Applications, Montpellier, France, Sep. 2-4, 2002; Field-Programmable Logic and Applications, Aug. 2022, 9 pages.
Guo et al., "A Systolic Array-Based FPGA Parallel Architecture for the BLAST Algorithm," International Scholarly Research Notices, Sep. 2012, 2012(1):195658, 13 pages.
Hach et al., "DeeZ: reference-based compression by local assembly," Nature Methods, Nov. 2014, 11(11):1082-1084.
Hach et al., "SCALCE: boosting sequence compression algorithms using locally consistent encoding, " Bioinformatics, Dec. 2012, 28(23):3051-3057.
Hall, "Short-Read DNA Sequence Alignment with Custom Designed FPGA-based Hardware," B.A., The University of Cambridge, 2007, Thesis for the degree of Master of Science, The University of British Columbia, Nov. 2010, 186 pages.
Hardcastle et al., "baySeq: Empirical Bayesian methods for identifying differential expression in sequence count data," BMC Bioginformatics, Aug. 2010, retrieved on May 25, 2016, retrieved from URL <http://bmcbioinformatics.biomedcentral.com/articles/10.1186/1471-2105-11-422>, 16 pages.
Harris et al., "A banded Smith-Waterman FPGA accelerator for mercury BLASTP", Paper, Presented at the 2007 International Conference on Field Programmable Logic and Applications, Amsterdam, Netherlands, Aug. 27-29, 2007; IEEE, Nov. 2007, 5 pages.
Hasan et al., "An Overview of Hardware-Based Acceleration of Biological Sequence Alignment," Computational Biology and Applied Bioinformatics, Sep. 2011, pp. 187-202.
Herbordt et al., "Single Pass Streaming BLAST on FPGAs", Parallel Comput. Nov. 2007, 33(10-11):741-756, NIH Public Access Author Manuscript, 25 pages.
Herbordt et al., "Single Pass, BLAST-like, Approximate String Matching of FPGAs," Boston University, 2006, 19 pages.
Hoang et al., "FPGA Implementation of Systolic Sequence Alignment," Paper, Presented at the International Conference on Field-Programmable Logic and Applications, Vienna, Austria, Aug. 31-Sep. 1992, 4 pages.
Hoang, "A Systolic Array for the Sequence Alignment Problem," Brown University, Apr. 1992, 25 pages.
Hoang, "Searching Genetic Databases on Splash 2," Paper, Presented at the Proceedings IEEE Workshop on FPGAs for Custom Computing Machines, Napa, California, Apr. 5-7, 1993; IEEE, published online Aug. 2002, pp. 185-191.
Holt et al., "MAKER2: an annotation pipeline and genome-database management tool for second-generation genome projects," BMC Bioinformatics, Dec. 2011, 12(1):1-4.
Homer et al., "BFAST: An Alignment Tool for Large Scale Genome Resequencing," PLOS One, Nov. 2009, retrieved on May 25, 2016, retrieved from URL <https://journals.plos.org/plosone/article?id=10.1371/journal.pone.0007767>, 11 pages.
Huang et al., "Hardware Acceleration of the Pair-HMM Algorithm for DNA Variant Calling," Proceedings of the 2017 ACM/SIGDA International Symposium on Field-Programmable Gate Arrays, Monterey, California, Feb. 22-24, 2017, pp. 275-284.
Hughey, "Parallel Hardware for Sequence Comparison And Alignment," Cabios, 1996, 12(6):473-479.
Hwang et al., "The mechanism of personalized service recommendation for the academic field," Paper, Presented at the 2017 4th International Conference on Computer Applications and Information Processing Technology (CAIPT), Kuta Bali, Indonesia, Aug. 8-10, 2017; IEEE, Mar. 2018, 5 pages.
IL Office Action in Israeli Appln. No. 263528, mailed on Jun. 22, 2023, 6 pages (with English translation).
IN Office Action in Indian Appln. No. 201827043970, mailed on Sep. 9, 2021, 6 pages (with English translation).
IN Office Action in Indian Appln. No. 202218018463, mailed on Sep. 26, 2024, 7 pages.
IN Office Action in Indian Appln. No. 202218018469, mailed on Sep. 26, 2024, 8 pages.

Iqbal et al., "De novo assembly and genotyping of variants using colored de Bruijn graphs," Nature Genetics, Feb. 2012, 44(2):226, 17 pages.
Isa et al., "A novel efficient FPGA architecture for HMMER acceleration," Paper, Presented at the 2012 International Conference on Reconfigurable Computing and FPGAs, Cancun, Mexico, Dec. 5-7, 2012; IEEE, Jan. 2013, 6 pages.
Jacob et al. "FPGA-Accelerated seed generation in Mercury BLASTP," Paper, Presented at the 15th Annual IEEE Symposium on Field-Programmable Custom Computing Machines (FCCM 2007), Napa, California, Apr. 23-25, 2007; IEEE, Sep. 2007, 10 pages.
Jacob et al., "Preliminary Results in Accelerating Profile HMM Search on FPGAs," Paper, Presented at the Sixth IEEE International Workshop on High Performance Computational Biology, Long Beach, California, Mar. 26-30, 2007; IEEE, Jun. 2007, 9 pages.
Jiang et al., "An efficient parallel implementation of the hidden markov methods for genomic sequence-search on a massively parallel system," IEEE Transactions on Parallel and Distributed Systems, Dec. 2007, 19(1):15-23.
JP Office Action in Japanese Appln. No. 2018-555440, dated Jan. 31, 2022, 4 pages (with English translation).
JP Notice of Allowance in Japanese Appln. No. 2018-555440, mailed on Jun. 12, 2023, 6 pages (with English translation).
JP Office Action in Japanese Appln. No. 2018-564374, mailed on Oct. 4, 2021, 7 pages (with English translation).
JP Office Action in Japanese Appln. No. 2022-046805, mailed on Jun. 5, 2023, 18 pages (with English translation).
JP Office Action in Japanese Appln. No. 2022-089149, mailed on Jun. 19, 2023, 9 pages (with English translation).
JP Office Action in Japanese Appln. No. 2022-515563, mailed on Oct. 7, 2024, 9 pages (with English translation).
JP Office Action in Japanese Appln. No. 2022-515895, mailed on Sep. 30, 2024, pages (with English translation).
JP Office Action in Japanese Appln. No. 2023-196840, mailed on Sep. 9, 2024, 6 pages (with English translation).
Kasap et al., "Design and Implementation of an FPGA-based Core for Gapped BLAST Sequence Alignment with the Two-Hit Method", Engineering Letters, Aug. 2008, 16(3):1-10.
KR Office Action in Korean Appln. No. 10-2024-7005077, mailed on Dec. 12, 2024, 19 pages (with English translation).
Lancaster et al., "Acceleration of Ungapped Extension in Mercury BLAST," Proceedings of the 7th Workshop on Media and Streaming Processors, Washington University, Nov. 2005, 9 pages.
Lancaster, "Design and Evaluation of a BLAST Ungapped Extension Accelerator, Master's Thesis, " Thesis for the degree of Master of Science, Washington University, May 2006, 79 pages.
Langmead et al., "Searching for SNPs with cloud computing," Genome Biology, Nov. 2009, 10:R134, 10 pages.
Lavenier, "SAMBA: Systolic Accelerator for Molecular Biological Applications," Research Report, RR-2845, INRIA, Mar. 1996, 22 pages.
Law et al., "Application of signal processing for DNA sequence compression", IET Signal Processing, Aug. 2019, 13(6):569-580.
Lee et al., "Clinical exome sequencing for genetic identification of rare Mendelian disorders," Jama, Nov. 2014, 312(18):1880-1887.
Lemoine et al., "High Speed Pattern Matching in Genetic Data Base with Reconfigurable Hardware," Paper, Presented at the Proceedings of the International Conference of Intelligent Systems for Molecular Biology, France, 1994, 2:269-275.
Li et al., "160-fold acceleration of the Smith-Waterman algorithm using a field programmable gate array (Fpga)," Bmc Bioinformatics, Jun. 2007, 8:185, 7 pages.
Liu et al., "An FPGA-Based Web Server for High Performance Biological Sequence Alignment," Paper, Presented at the 2009 NASA/ESA Conference on Adaptive Hardware and Systems, San Francisco, California, Jul. 29-Aug. 1, 2009; IEEE, Nov. 2009, pp. 361-368.
Liu et al., "Bisulfite-free direct detection of 5-methylcytosine and 5-hydroxymethylcytosine at base resolution," Nature Biotechnology, Apr. 2019, 37(4):424-429.
Lloyd et al., "Hardware Accelerated Sequence Alignment with Traceback," International Journal of Reconfigurable Computing, 2009, 2009:762362, 11 pages.

(56) References Cited

OTHER PUBLICATIONS

Lopresti, "Rapid Implementation of a Genetic Sequence Comparator Using Field-Programmable Logic Arrays," Advanced Research in VLSI, 1991, pp. 138-152.
Luethy et al., "Hardware and software systems for accelerating common bioinformatics sequence analysis algorithms," Drug Discovery Today: BIOSILICO, Jan. 2004, 2(1):12-17.
Madhavan et al., "Race Logic: A Hardware Acceleration for Dynamic Programming Algorithms," Paper, Presented at the 2014 ACM/IEEE 41st International Symposium on Computer Architecture (ISCA), Minneapolis, Minnesota, Jun. 14-18, 2014; IEEE, Jul. 2014, 12 pages.
Mahram, "FPGA Acceleration of Sequence Analysis Tools in Bioinformatics," Dissertation for the degree of Doctor of Philosophy, Boston University, College of Engineering, 2013, 180 pages.
Mandelker et al., "Navigating highly homologous genes in a molecular diagnostic setting: a resource for clinical next-generation sequencing," Genetics in Medicine, Dec. 2016, 18(12):1282-1289.
Maxfield, "Impulse achieves 16X speed-up of genome analysis on $2,500 FPGA module," EE Times, Jun. 15, 2012, retrieved on Mar. 29, 2016, retrieved from URL <http://www.eetimes.com/documentasp?docid=1317288&print=yes>, 4 pages.
McKenna et al., "The Genome Analysis Toolkit: a MapReduce framework for analyzing next-generation DNA sequencing data," Genome Research, Sep. 2010, 20(9):1297-1303.
Mikami et al., "Efficient FPGA-based Hardware Algorithms for Approximate String Matching," Paper, Presented at the 23rd International Technical Conference on Circuits/Systems, Computers and Communications (ITC-CSCC), Yamaguchi, Japan, Jul. 6-9, 2008, pp. 201-204.
Miller et al., "A 26-hour system of highly sensitive whole genome sequencing for emergency management of genetic diseases," Genome Medicine, Sep. 2015, 7:100, 16 pages.
Mishra, "Gappy TotalReCaller for RNASeq Base-Calling and Mapping," bioRxiv:000489, Jan. 2013, 10 pages.
Moritz et al., "Implementation of a Parallel Algorithm for Protein Pairwise Alignment Using Reconfigurable Computing, " Paper, Presented at the 2006 IEEE International Conference on Reconfigurable Computing and FPGA's (ReConFig 2006), San Luis Potosi, Mexico, Sep. 20-22, 2006; IEEE, Feb. 2007, 7 pages.
Muriki et al., "RC-BLAST: Towards a Portable, Cost-Effective Open Source Hardware Implementation," Paper, Presented at the 19th IEEE International Parallel and Distributed Processing Symposium, Denver, Colorado, Apr. 4-8, 2005; IEEE, Apr. 2005, 8 pages.
MX Office Action in Mexican Appln. No. MX/a/2018/008527, mailed on May 25, 2023, 9 pages (with English translation).
MY Office Action in Malaysian Appln. No. PI 2018702376, mailed on Jun. 17, 2022, 3 pages.
Nagasaki et al., "DDBJ read annotation pipeline: a cloud computing-based pipeline for high-throughput analysis of next-generation sequencing data," DNA Research, Aug. 2013, 20(4):383-90.
Nalbantoglu et al., "Compression of Next Generation Sequencing Data," DCC, Apr. 2015, 10 pages.
Nawaz et al., "A Parallel FPGA Design of the Smith-Waterman Traceback," Paper, Presented at the 2010 International Conference on Field-Programmable Technology, Beijing, China, Dec. 8-10, 2010; IEEE, Jan. 2011, 6 pages.
Nawaz et al., "Fast Smith-Waterman hardware implementation," Paper, Presented at the 2010 IEEE International Symposium on Parallel & Distributed Processing, Workshops and Phd Forum (IPDPSW), Atlanta, Georgia, Apr. 19-23, 2010; IEEE, May 2010, 4 pages.
Nelson et al., "Shepard: A Fast Exact Match Short Read Aligner," Paper, Presented at the Tenth ACM/IEEE International Conference on Formal Methods and Models for Codesign (MEMCODE2012), Arlington, Virginia, Jul. 16-17, 2012; IEEE, Sep. 2012, 4 pages.
NZ Office Action in New Zealand Appln. No. 784186, mailed on Jun. 29, 2023, 3 pages.

NZ Office Action in New Zealand Appln. No. 784189, mailed on Feb. 13, 2024, 7 pages.
NZ Office Action in New Zealand Appln. No. 784189, mailed on Jun. 27, 2023, 3 pages.
NZ Office Action in New Zealand Appln. No. 789137, mailed on Mar. 5, 2024, 2 pages.
NZ Office Action in New Zealand Appln. No. 789138, mailed on Mar. 13, 2024, 2 pages.
NZ Office Action in Russian Appln. No. 743311, mailed on Jun. 21, 2023, 3 pages.
NZ Office Action in Russian Appln. No. 748612, mailed on Dec. 15, 2023, 3 pages.
Oliver et al., "High performance database searching with HMMer on FPGAs," Paper, Presented at the 2007 IEEE International Parallel and Distributed Processing Symposium, Long Beach, California, Mar. 26-30, 2007; IEEE, Jun. 2007, 7 pages.
Oliver et al., "Multiple Sequence Alignment on an FPGA," Paper, Presented at the 11th International Conference on Parallel and Distributed Systems (ICPADS'05), Fukuoka, Japan, Jul. 20-22, 2005; IEEE, Nov. 2005, 5 pages.
Oliver et al., "Using Reconfigurable Hardware to Accelerate Multiple Sequence Alignment with ClustalW," BioInformatics, May 2005, 21(162):3431-3432.
Oliver et al., "A Reconfigurable Computing System Based on a Cache-Coherent Fabric," Paper, Presented at the 2011 International Conference on Reconfigurable Computing and FPGAs, Cancun, Mexico, Nov. 30-Dec. 2, 2011; IEEE, Jan. 2012, 6 pages.
Oliver et al., "Integrating FPGA acceleration into HMMer," Parallel Computing, Sep. 2008, 34:681-691.
Oliver, "Hyper Customized Processors for Bio-Sequence Database Scanning on FPGAs," Paper, Presented at the FPGA '05: Proceedings of the 2005 ACM/SIGDA 13th International Symposium on Field-Programmable Gate Arrays, Monterey, California, Feb. 20-22, 2005; Association for Computing Machinery, Feb. 2005, pp. 229-237.
Olson et al., "Hardware Acceleration of Short Read Mapping, " Paper, Presented at the 2012 IEEE 20th International Symposium on Field-Programmable Custom Computing Machines, Toronto, Canada, Apr. 29-May 1, 2012; IEEE, Jul. 2012, 8 pages.
Olson, "An FPGA Acceleration of Short Read Human Genome Mapping," thesis for the degree of Master of Science in Electrical Engineering, University of Washington, 2011, 103 pages.
PCT International Preliminary Report on Patentability in International Appln. No. PCT/US2020/050584, mailed on Nov. 25, 2021, 9 pages.
PCT International Preliminary Report on Patentability in International Appln. No. PCT/US2020/050586, mailed on Nov. 25, 2021, 13 pages.
PCT International Search Report and Written Opinion in International Appln. No. PCT/US2016/020480, mailed on May 17, 2016, 6 pages.
PCT International Search Report and Written Opinion in International Appln. No. PCT/US2016/026796, mailed on Jul. 18, 2016, 8 pages.
PCT International Search Report and Written Opinion in International Appln. No. PCT/US2016/040842, mailed on Oct. 4, 2016, 10 pages.
PCT International Search Report and Written Opinion in International Appln. No. PCT/US2016/18765, mailed on May 6, 2016, 9 pages.
PCT International Search Report and Written Opinion in International Appln. No. PCT/US2017/013057, mailed on Apr. 11, 2017, 10 pages.
PCT International Search Report and Written Opinion in International Appln. No. PCT/US2017/036424, mailed on Sep. 12, 2017, 12 pages.
PCT International Search Report and Written Opinion in International Appln. No. PCT/US2017/040385, mailed on Oct. 27, 2017, 15 pages.
PCT International Search Report and Written Opinion in International Appln. No. PCT/US2017/058890, mailed on Feb. 23, 2018, 16 pages.

(56) References Cited

OTHER PUBLICATIONS

PCT International Search Report and Written Opinion in International Appln. No. PCT/US2020/050584, mailed on Nov. 20, 2020, 16 pages.
PCT International Search Report and Written Opinion in International Appln. No. PCT/US2020/050586, mailed on Nov. 26, 2020, 16 pages.
PCT International Search Report and Written Opinion in International Appln. No. PCT/US2021/058364, mailed on Feb. 23, 2022, 19 pages.
PCT International Search Report and Written Opinion in International Appln. No. PCT/US2024/031054, mailed on Nov. 12, 2024, 9 pages.
PCT International Search Report and Written Opinion in International Appln. No. PCT/US2024/031062, mailed on Aug. 22, 2024, 11 pages.
PCT International Search Report in International Appln. No. PCT/US2014/012144, mailed on Jun. 18, 2014, 2 pages.
Peltenburg et al., "Maximizing systolic array efficiency to accelerate the PairHMM Forward Algorithm," Paper, Presented at the 2016 IEEE International Conference on Bioinformatics and Biomedicine (BIBMJ, IEEE), Shenzhen, China, Dec. 15-18, 2016; IEEE, Jan. 2017, pp. 758-762.
Raphael et al., "A novel method for multiple alignment of sequences with repeated and shuffled elements," Genome Research, Nov. 2004, 14(11):2336-2346.
Ren et al., "FPGA acceleration of the pair-HMMs forward algorithm for DNA sequence analysis," Paper, Presented at the 2015 IEEE International Conference on Bioinformatics and Biomedicine (BIBM), Washington D.C., USA, Nov. 9-12, 2015; IEEE, Dec. 2015, 6 pages.
Rimmer et al., "Integrating mapping-, assembly-and haplotype-based approaches for calling variants in clinical sequencing applications," Nature Genetics, Aug. 2014, 46(8):912-918.
RU Office Action in Russian Appln. No. 2021118824, mailed on Oct. 17, 2022, 21 pages (with English translation).
RU Office Action in Russian Appln. No. 2021134292, dated Nov. 23, 2022, 13 pages (with English translation).
RU Office Action in Russian Appln. No. 2022101850, mailed on Nov. 25, 2022, 11 pages (with English translation).
RU Office Action in Russian Appln. No. 2022101852, mailed on Jan. 31, 2023, 13 pages (with English translation).
Ruffalo et al., "Comparative analysis of algorithms for nextgeneration sequencing read alignment," Bioinformatics, Aug. 2011, 27(20): 2790-2796, retrieved on May 25, 2016, retrieved from URL <https://bioinformatics.oxfordjournals.org/content/27/20/2790.full>, 12 pages.
Russell, "TGAC Unleashes DRAGEN to Accelerate Genomics Workflows, " HPC Wire, Oct. 28, 2015, retrieved on Apr. 12, 2022, retrieved from URL <https://www.hpcwire.com/2015/10/28/tgac-unleashes-dragen-to-accelerate-genomics-workflows/>, 12 pages.
Sarkar et al., "Network-on-Chip Hardware Accelerators for Biological Sequence Alignment," IEEE Transactions on Computers, Jan. 2010, 59(1):29-41.
Schatz et al., "Cloud Computing and the DNA Data Race," Nature Biotechology, Jul. 2010, 28(7):691-693 (HHS Public Access Author Manuscript).
Schatz et al., "High-throughput sequence alignment using Graphics Processing Units," BMC Bioinformatics, Dec. 2007, retrieved on May 25, 2016, retrieved from URL <http://bmcbioinformatics.biomedcentral.com/articles/10.1186/1471-2105-8-474>, 13 pages.
Schatz, "CloudBurst: highly sensitive read mapping with MapReduce," Bloinformatics, Apr. 2009, 25(11):1363-1369, retrieved on May 25, 2016, retrieved from URL <http:///bioinformatics.oxfordioumals.ora/content/25/11/1363.full>, 14 pages.
Settle et al., "High-Performance Dynamic Programming on FPGAs with OpenCL," Paper, Presented at the 2013 IEEE High Performance Extreme Computing Conference (HPEC), Waltham, Massachusets, Sep. 10-12, 2013; IEEE, 2013, 6 pages.
SG Office Action in Singaporean Appln. No. 11201805562Q, mailed on Oct. 26, 2022, 5 pages.
SG Office Action in Singaporean Appln. No. 11202200666W, mailed on Feb. 28, 2025, 9 pages.
Sotiriades et al., "FPGA based Architecture for DNA Sequence Comparison and Database Search," Paper, Presented at the Proceedings 20th IEEE International Parallel & Distributed Processing Symposium, Rhodes, Greece, Apr. 25-29, 2006; IEEE, Jun. 2006, 8 pages.
Sotiriades et al., "Some Initial Results on Hardware BLAST acceleration with a Reconfigurable; Architecture," Paper, Presented at the Proceedings 20th IEEE International Parallel & Distributed Processing Symposium, Rhodes, Greece, Apr. 25-29, 2006; IEEE, Jun. 2006, 8 pages.
Sun et al., "Accelerating HMMer on FPGAs using systolic array based architecture," Paper, Presented at the 2009 IEEE International Symposium on Parallel & Distributed Processing, Rome, Italy, May 23-29, 2009; IEEE, Jul. 2009, 8 pages.
Tang et al., "Accelerating Millions of Short Reads Mapping on a Heterogeneous Architecture with FPGA Accelerator," Paper, Presented at the 2012 IEEE 20th International Symposium on Field-Programmable Custom Computing Machines, Toronto, Canada, Apr. 29-May 1, 2012; IEEE, Jul. 2012, pp. 184-187.
Timelogic, "Accelerated BLAST Performance with Tera-Blast: a comparison of FPGA versus GPU and CPU Blast implementations," Technical Note, May 2013, Version 1.0, 5 pages.
Treangen et al., "Gapped extension for local multiple alignment of interspersed DNA repeats," Paper, Presented at the ISBRA International Symposium on Bioinformatics Research and Applications 2008, Atlanta, Georgia, May 6-8, 2008; Bioinformatics Reasearch and Applications, 2008, 4983:74-86.
US Office Action in U.S. Appl. No. 15/048,935, mailed on Sep. 14, 2021, 21 pages.
US Office Action in U.S. Appl. No. 15/616,833, mailed on Apr. 4, 2019, 6 pages.
US Office Action in U.S. Appl. No. 15/643,381, mailed on Jan. 22, 2018, 9 pages.
US Office Action in U.S. Appl. No. 15/907,263, mailed on May 3, 2018, 6 pages.
US Office Action in U.S. Appl. No. 15/915,013, mailed on Oct. 2, 2020, 5 pages.
US Office Action in U.S. Appl. No. 16/120,103, mailed on Oct. 5, 2020, 5 pages.
US Office Action in U.S. Appl. No. 16/567,201, mailed on Sep. 14, 2023, 17 pages.
US Office Action in U.S. Appl. No. 17/165,900, mailed on Dec. 13, 2024, 5 pages.
US Office Action in U.S. Appl. No. 17/165,900, mailed on Jun. 20, 2024, 10 pages.
US Office Action in U.S. Appl. No. 17/520,615, mailed on Feb. 18, 2022, 5 pages.
US Office Action in U.S. Appl. No. 17/974,978, mailed on Mar. 6, 2023, 6 pages.
US Office Action in U.S. Appl. No. 18/540,814, mailed on Sep. 23, 2024, 32 pages.
Van Court et al., "Families of FPGA-Based Algorithms for Approximate String Matching," Paper, Presented at the 15th IEEE International Conference on Application-Specific Systems, Architectures and Processors, Galveston, Texas, Sep. 29, 2024; IEEE, Oct. 2004, 11 pages.
Van Der Auwera et al., "From FastQ data to high confidence variant calls: the Genome Analysis Toolkit best practices pipeline," Current Portocols in Bioinformatics, Oct. 2013, 11(1110):11.10.1-11.0.33 (HHS Public Access Author Manuscript), 27 pages.
Wan et al., "Transformations for the compression of FASTQ quality scores of next-generation sequencing data," Bioinformatics, Mar. 2012, 28(5):628-635.
Wandelt et al., "Adaptive efficient compression of genomes," Algorithms For Molecular Biology, Nov. 2012, 7:30, 9 pages.
Wandelt et al., "FRESCO: Referential compression of highly similar sequences," IEEE/ACM Transactions on Computational Biology and Bioinformatics, Oct. 2013, 10(5):1275-1288.
Wang et al., "Heterogeneous cloud framework for big data genome sequencing," IEEE/ACM Transactions on Computational Biology and Bioinformatics, Sep. 2014, 12(1):166-78.

(56) References Cited

OTHER PUBLICATIONS

Wikipedia.org [online], "Arithmetic coding," Oct. 29, 2020, retrieved on Feb. 15, 2022, retrieved from URL <https://en.wikipedia.org/w/index.php?title=Arithmetic_coding&oldid=985967562>, 14 pages.

Wikipedia.org [online], "CpG site," Jul. 24, 2021, retrieved on Jan. 16, 2025, retrieved from URL <https://en.wikipedia.org/wiki/CpG_site>, 15 pages.

Wilke et al., "A RESTful API for accessing microbial community data for MG-RAST," PLoS Computational Biology, Jan. 8, 2015, 11(1):e1004008, 8 pages.

Wu et al., "Sequence analysis: GMAP: a genomic mapping and alignment program for mRNA and EST sequences," Bioinformatics, Feb. 2005, 21(92005):1859-1875.

Yamaguchi et al., "High Speed Homology Search with FPGAs," Paper, Presented at the Pacific Symposium On Biocomputing, Kauai, Hawaii, Jan. 3-7, 2002, 7:271-282.

Yu et al., "A Smith-Waterman Systolic Cell," Paper, Presented at the International Conference on Field Programmable Logic and Applications, Lisbon, Portugal, Sep. 1-3, 2003; Field Programmable Logic and Application, Jan. 2003, pp. 375-384.

ZA Notice of Acceptance in South African Appln. No. 2022/10297, mailed on Jun. 5, 2023, 2 pages.

Zhang et al., "A Practical Comparison of De Novo Genome Assembly Software Tools for Next-Generation Sequencing Technologies," PLOS One, Mar. 2011, retrieved on May 25, 2016, retrieved from URL <http://journals.plos.org/plosone/article?id=10.1371/journal.pone.0017915>, 10 pages.

Zhang et al., "Implementation of the Smith-Waterman algorithm on a reconfigurable supercomputing platform," Proceedings of the 1st international workshop on High-performance reconfigurable computing technology and applications: held in conjunction with SC07, Nov. 11, 2007, 39, 19 pages.

Zhang et al., "Joint haplotype phasing and genotype calling of multiple individuals using haplotype informative reads," Bioinformatics, Oct. 2013, 29(19):2427-2434.

Zyuzin et al., "Approach to Compression DNA Sequences Using an Algorithm Binary Achiever," Materials of Scientific and Practical Internet Conferences, Nov. 25-26, 2014, 5 pages.

* cited by examiner

MULTI-PASS SOFTWARE-ACCELERATED GENOMIC READ MAPPING ENGINE

CROSS-REFERENCE TO RELATED APPLICATION

This application claims the benefit of U.S. Provisional Application No. 63/317,859, filed Mar. 8, 2022, the contents of which are incorporated by reference herein.

BACKGROUND

In some cases, genomic read mapping describes a method to identify the locus of a gene and the distances between genes. Computers can be used to analyze one or more sets of genomic data and correlate a collection of molecular markers, such as a series of nucleotides, with their respective positions on a given reference genome. In this way, a computer can be used to "map" the collection of molecular markers onto the reference genome.

SUMMARY

In some implementations, a system for multi-pass accelerated genomic read mapping includes one or more processing stages. Each of the one or more processing stages can include extracting one or more k-mers from a genomic data read and processing those k-mers to determine candidate alignment locations that indicate a location on a reference genome at which to align the genomic data read. In some implementations, a first processing stage includes generating a single filtered k-mer, generating a candidate alignment corresponding to reference genomic data, and evaluating the candidate alignment to determine if the alignment satisfies alignment criteria. If the candidate alignment generated in the first processing stage does not satisfy alignment criteria, a system can execute a second processing stage. If one or more candidate alignment locations generated in the second processing stage do not satisfy alignment criteria, a system can execute a third processing stage. In some implementations, processing stops when a candidate alignment that satisfies alignment criteria is evaluated.

In some implementations, alignment criteria includes a threshold amount of mismatches between a portion of the genomic data read and a portion of a reference genomic data read. In some implementations, a k-mer seed is defined as a sequence of sequential nucleotides where the number of nucleotides in the sequence for a given k-mer is defined by "k" and the nucleotides (or, more generally, bases) are represented by strings of letters from a defined vocabulary. For example, a given k-mer may represent the sequence "ATGCG" where the symbols: {A, C, G, T} represent the four types of nucleotides present in deoxyribonucleic acid (DNA), namely Adenine, Cytosine, Guanine, and Thymine.

In some implementations, a genomic data read includes data indicating a sequence of nucleotides. A sequence of nucleotides can include a sequence of symbols, each representing chemical compounds. For example, genomic data read can include symbols A, C, G, and T representing four types of nucleotides present in deoxyribonucleic acid (DNA), namely Adenine, Cytosine, Guanine, and Thymine. In ribonucleic acid (RNA), Thymine is replaced by Uracil (U).

In some implementations, a genomic signature includes a hash generated using a hash function applied to a k-mer. For example, a system can obtain a k-mer representing the sequence "ATGCG". The system can apply a hash function on the data of the k-mer. In some implementations, the resulting hash is used as a key to query a hash table.

In some implementations, predetermined criteria used to select a subset of k-mer seeds includes value matching. For example, a system can perform one or more modulo operations on one or more genomic signatures generated based on a hash function applied to one or more k-mers. The system can compare the results of the one or more modulo operations to a value as part of a predetermined criteria. If the results match values specified in the predetermined criteria, the system can select the subset of k-mer seeds.

In some implementations, a reference sequence location includes a location of a k-mer within a reference genome. For example, the sequence "ATGCG" can appear starting at the $300^{th}$ nucleotide in a reference genome. The sequence may appear in one or more locations within the reference genome. The reference sequence locations for one or more k-mers can be stored in a hash table.

One innovative aspect of the subject matter described in this specification is embodied in a method that includes obtaining, by one or more computers, a first k-mer seed from a genomic data read; generating, by the one or more computers, a genomic signature based on a first k-mer seed; determining, by the one or more computers, a reference sequence location that matches at least a portion of the first k-mer seed using a hash data structure, where the hash data structure includes N data cells including a first portion storing a predetermined genomic signature and a second portion storing a value that corresponds to a location within a reference genomic sequence that matches at least a portion of the first k-mer seed from which the predetermined genomic signature was derived; determining, by the one or more computers, a number of mismatches based on comparing genomic data of the genomic data read to genomic data of the reference genomic sequence; based on determining the number of mismatches includes one or more mismatches, obtaining, by the one or more computers, a set of k-mer seeds from the genomic data read; and based on the set of k-mer seeds from the genomic data read, selecting, by the one or more computers, an actual alignment for the genomic data read.

Other implementations of this and other aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The foregoing and other embodiments can each optionally include one or more of the following features, alone or in combination. For instance, in some implementations obtaining the first k-mer seed from the genomic data read includes obtaining a first k bases of the genomic data read as the first k-mer seed.

In some implementations, actions include, based on determining the number of mismatches is zero, selecting the first k-mer seed as the actual alignment for the genomic data read.

In some implementations, actions include generating genomic signatures for each k-mer seed of the set of k-mer seeds; and selecting a subset of the set of k-mer seeds based on the genomic signatures.

In some implementations, selecting the subset of the set of k-mer seeds based on the genomic signatures includes performing one or more modulo operations including a modulo operation on each genomic signature of the genomic signatures; and selecting the subset of the set of k-mer seeds based on results of the one or more modulo operations and a predetermined criteria.

In some implementations, actions include determining, by the one or more computers, a reference sequence location for each k-mer seed of the subset that matches at least a portion of the given k-mer seed using the hash data structure; and generating a candidate location list including a reference sequence location for each k-mer seed of the subset.

In some implementations, actions include sorting the reference sequence locations of the candidate location list according to a number of k-mer seeds paired with the given reference sequence location in the hash data structure; and determining a number of mismatches for each of the reference sequence locations of the sorted candidate location list compared to the reference genomic sequence in the order of the sorted candidate location list.

In some implementations, actions include determining a number of mismatches for a first candidate location of the reference sequence locations of the sorted candidate location list satisfies a mismatch threshold; and selecting the first candidate location as the actual alignment.

In some implementations, the mismatch threshold includes a threshold number of mismatching nucleotide values.

In some implementations, actions include determining a number of mismatches for one or more candidate locations of the reference sequence locations of the sorted candidate location list do not satisfy a mismatch threshold; and based on determining the number of mismatches do not satisfy the mismatch threshold, obtaining a second set of k-mer seeds from the genomic data read.

In some implementations, actions include generating second genomic signatures for each k-mer seed of the second set of k-mer seeds; performing second one or more modulo operations including a modulo operation on each genomic signature of the second genomic signatures; and selecting a second subset of the second set of k-mer seeds based on results of the second one or more modulo operations and a predetermined criteria.

In some implementations, actions include determining a reference sequence location for each k-mer seed of the second subset that matches at least a portion of the given k-mer seed using the hash data structure; and generating a second candidate location list including a reference sequence location for each k-mer seed of the second subset.

In some implementations, actions include sorting the reference sequence locations of the second candidate location list according to a number of k-mer seeds paired with the given reference sequence location in the hash data structure; and determining a number of mismatches for each of the reference sequence locations of the sorted second candidate location list compared to the reference genomic sequence in the order of the sorted second candidate location list.

In some implementations, actions include determining a number of mismatches for a second candidate location of the reference sequence locations of the sorted second candidate location list satisfies a second mismatch threshold; and selecting the second candidate location as the actual alignment.

Another innovative aspect of the subject matter described in this specification is embodied in a method that includes obtaining, by one or more computers, a first k-mer seed from a genomic data read; generating, by the one or more computers, a genomic signature based on the first k-mer seed; determining, by the one or more computers, a reference sequence location that matches at least a portion of the first k-mer seed using a hash data structure, wherein the hash data structure comprises N data cells comprising a first portion storing a predetermined genomic signature and a second portion storing a value that corresponds to a location within a reference genomic sequence that matches at least the portion of the first k-mer seed from which the predetermined genomic signature was derived; determining, by the one or more computers, a number of mismatches based on comparing genomic data of the genomic data read to genomic data of the reference genomic sequence; determining, by the one or more computers, the number of mismatches does not satisfy a mismatch threshold; based on determining the number of mismatches does not satisfy the mismatch threshold, obtaining, by the one or more computers, a second set of k-mer seeds from the genomic data read; and based on the second set of k-mer seeds from the genomic data read, selecting, by the one or more computers, an actual alignment for the genomic data read.

Other implementations of this and other aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The foregoing and other embodiments can each optionally include one or more of the following features, alone or in combination. For instance, in some implementations, 2. The method of claim 1, wherein obtaining the first k-mer seed from the genomic data read includes obtaining a first k bases of the genomic data read as the first k-mer seed.

In some implementations, selecting the actual alignment for the genomic data read based on the second set of k-mer seeds from the genomic data read includes generating genomic signatures for each k-mer seed of the second set of k-mer seeds; and selecting a subset of the second set of k-mer seeds based on the genomic signatures.

In some implementations, selecting the subset of the second set of k-mer seeds based on the genomic signatures includes performing one or more modulo operations including a modulo operation on each genomic signature of the genomic signatures; and selecting the subset of the second set of k-mer seeds based on results of the one or more modulo operations and a predetermined criterion.

In some implementations, actions include determining, by the one or more computers, a reference sequence location for each k-mer seed of the second set of k-mer seeds that matches at least a portion of a given k-mer seed using the hash data structure; and generating a candidate location list including a reference sequence location for each k-mer seed of the second set of k-mer seeds.

In some implementations, actions include sorting the reference sequence locations of the candidate location list according to a number of k-mer seeds paired with the given reference sequence location in the hash data structure; and determining a number of mismatches for each of the reference sequence locations of the sorted candidate location list compared to the reference genomic sequence in an order of the sorted candidate location list.

In some implementations, actions include determining a number of mismatches for a first candidate location of the reference sequence locations of the sorted candidate location list satisfies a second mismatch threshold; and selecting the first candidate location as the actual alignment.

In some implementations, the second mismatch threshold includes a threshold number of mismatching nucleotide values.

In some implementations, actions include generating second genomic signatures for each k-mer seed of the second set of k-mer seeds; performing second one or more modulo operations including a modulo operation on each genomic signature of the second genomic signatures; and selecting a second subset of the second set of k-mer seeds based on results of the second one or more modulo operations and a predetermined criterion.

In some implementations, actions include determining a reference sequence location for each k-mer seed of the second subset that matches at least a portion of a given k-mer seed using the hash data structure; and generating a second candidate location list including a reference sequence location for each k-mer seed of the second subset.

In some implementations, actions include sorting the reference sequence locations of the second candidate location list according to a number of k-mer seeds paired with the given reference sequence location in the hash data structure; and determining a number of mismatches for each of the reference sequence locations of the sorted second candidate location list compared to the reference genomic sequence in an order of the sorted second candidate location list.

In some implementations, actions include determining a number of mismatches for a second candidate location of the reference sequence locations of the sorted second candidate location list satisfies a third mismatch threshold; and selecting the second candidate location as the actual alignment.

A third innovative aspect of the subject matter described in this specification is embodied in a method that includes obtaining, by one or more computers, a first k-mer seed from a genomic data read; generating, by the one or more computers, a genomic signature based on the first k-mer seed; determining, by the one or more computers, a reference sequence location that matches at least a portion of the first k-mer seed using a hash data structure, wherein the hash data structure comprises N data cells comprising a first portion storing a predetermined genomic signature and a second portion storing a value that corresponds to a location within a reference genomic sequence that matches at least a portion of the first k-mer seed from which the predetermined genomic signature was derived; determining, by the one or more computers, a number of mismatches based on comparing genomic data of the genomic data read to genomic data of the reference genomic sequence; comparing the number of mismatches to a mismatch threshold; and based on comparing the number of mismatches to the mismatch threshold, selecting, by the one or more computers, an actual alignment for the genomic data read. In some implementations, selecting an actual alignment for the genomic data read occurs subsequent to comparing the number of mismatches to the mismatch threshold.

Other implementations of this and other aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The foregoing and other embodiments can each optionally include one or more of the following features, alone or in combination. For instance, in some implementations, actions include determining the number of mismatches satisfies the mismatch threshold, wherein selecting the actual alignment for the genomic data read includes selecting the reference sequence location that matches at least a portion of the first k-mer seed.

In some implementations, actions include determining the number of mismatches does not satisfy the mismatch threshold; and obtaining a second k-mer seed from the genomic data read, wherein selecting the actual alignment for the genomic data read includes selecting a reference sequence location that matches at least a portion of the second k-mer seed.

In some implementations, actions include determining the reference sequence location that matches at least a portion of the second k-mer seed using the hash data structure.

A fourth innovative aspect of the subject matter described in this specification is embodied in a method that includes extracting k-mer seeds from obtained genomic data; generating a filtered set of the k-mer seeds; and storing the filtered set of the k-mer seeds in a hash data structure.

Other implementations of this and other aspects include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The foregoing and other embodiments can each optionally include one or more of the following features, alone or in combination. For instance, in some implementations, generating the filtered set of the k-mer seeds includes generating one or more hash values for each of the k-mer seeds; and filtering the k-mer seeds using the one or more hash values.

In some implementations, generating the filtered set of the k-mer seeds includes determining a number of occurrences of the k-mer seeds; and filtering the k-mer seeds using the number of occurrences.

In some implementations, the hash data structure comprises N data cells comprising a first portion storing a predetermined genomic signature for a k-mer seed of the k-mer seeds and a second portion storing a value that corresponds to a location within a reference genomic sequence that matches at least a portion of the k-mer seed from which the predetermined genomic signature was derived.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION

The present disclosure is directed to a multi-pass software accelerated genomic data mapping engine. The multi-pass software accelerated genomic data mapping engine provides an important technological improvement in that the multi-pass software accelerated algorithm enables an iterative evaluation of k-mer seeds against candidate alignments stored in a hash table. As a result of the iterative evaluation, the present disclosure is able to terminate the mapping process early before all of the k-mers of a particular genomic data read are evaluated. This technological improvement reduces the runtime of mapping and aligning genomic data reads of a biological samples to a reference genome. Accordingly, significant gains in efficiency can be achieved in any applications that use the genomic data mapping engine to perform mapping and aligning operations. Such operations may include, but are not limited to, for example, genomic data compression algorithms, which can achieve faster compression speeds and higher compression ratios relative to conventional software-accelerated mapping engines.

Based on the implementation, design tradeoffs can be made between speed, compression ratio, and size of the generated hash table. For example, in some implementations, a smaller k-mer seed size can result in generation of smaller hash table. Such implementations may be particularly beneficial when data storage on a computer running the multi-pass genomic mapping engine is limited. In such instances, however, it may be comparatively slower to identify an actual alignment relative implementations that utilize a larger k-mer seed size. Alternatively, in other implementations, a larger k-mer seed size can result in a larger hash table, but enable the identification of an actual alignment of a genomic data read faster. In either scenario, however, the present disclosure enables a technological improvement of either efficient use of storage space or reduced runtime. In certain implementations, an improvement can be achieved in both domains by finding the preferred balance of k-mer seed size and execution speed. For example, experimentation has shown that a k-mer seed size of 22 base calls can yield such balanced performance.

Figure 1:
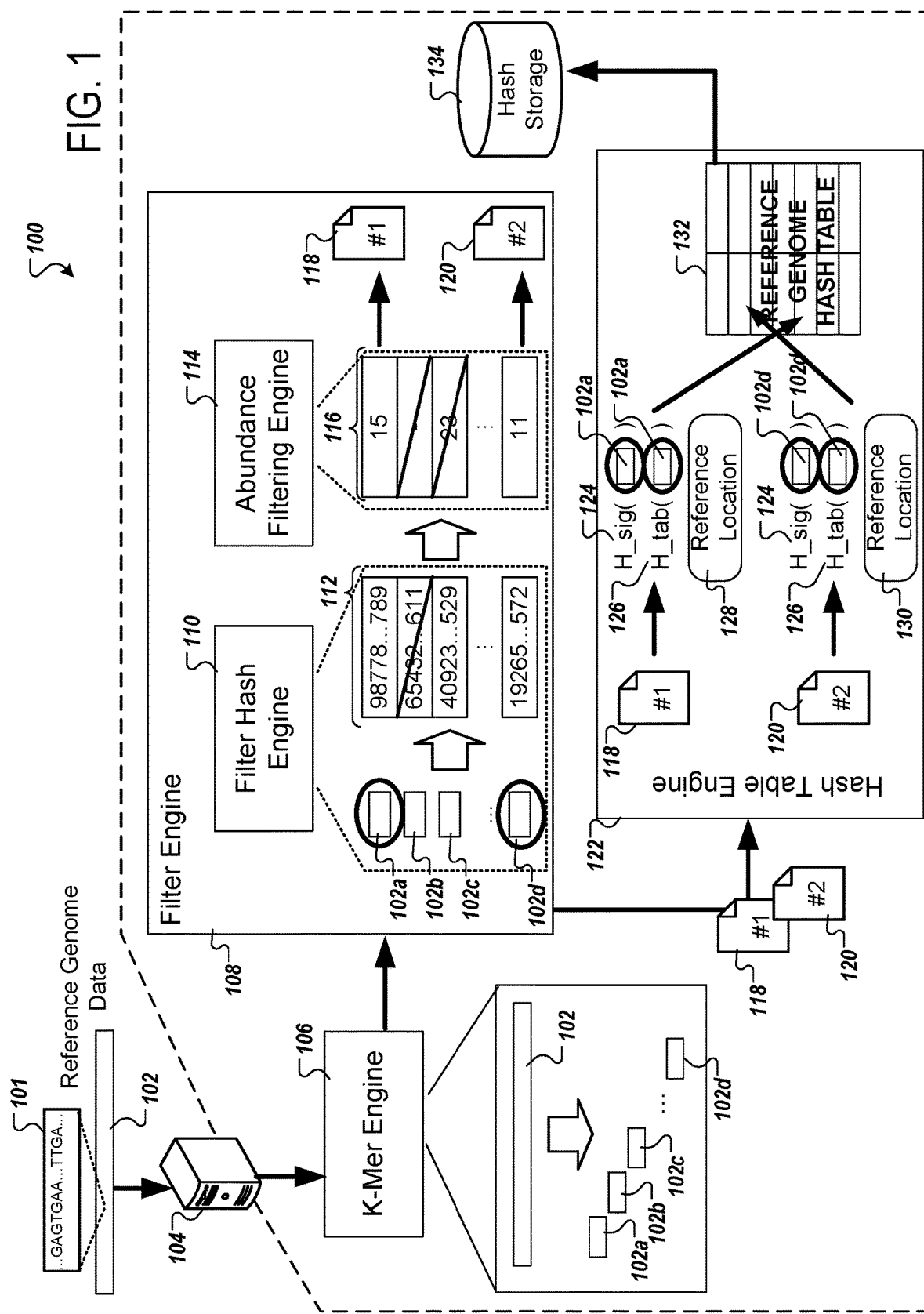
FIG. 1 is a diagram showing an example of a system for generating a hash table for a multi-pass software accelerated genomic read mapping engine.

FIG. 1 is a diagram showing an example of a system 100 for generating a hash table for software accelerated genomic read mapping engine. The system 100 includes a computer 104. In some implementations, the computer 104 performs one or more operations of one or more of a K-mer engine 106, a filter engine 108, and a hash table engine 122. The computer 104 can be, for example, a tablet computer, a desktop computer, a server computer, multiple server computers, a nucleic acid sequencing device, or any other computing device(s). In other implementations, the computer 104 is communicably connected to one or more other computers configured to perform operations of one or more of the K-mer engine 106, the filter engine 108, and the hash table engine 122. These computers can be of the same, or different, type of computer as computer 104.

In some implementations, the computer 104 includes a portion of memory storage assigned to hash storage 134. In some implementations, the computer 104 is communicably connected to a computer configured with one or more memory devices for hash storage 134. For example, the computer 104 can be communicably connected to a server. The server can store the hash storage 134. The computer 104 can access the hash storage 134 on memory storage of the server.

The computer 104 obtains reference genome data 102. The reference genome data 102 can include a reference genome (which may also be referred to herein as a reference sequence) such as a DNA sequence assembled for an organism by one or more scientists. The reference genome data 102 can include data indicating a sequence of a plurality of nucleotides. For example, the reference genome data 102 can include symbols A, C, G, and T representing four types of nucleotides present in deoxyribonucleic acid (DNA), namely Adenine (A), Cytosine (C), Guanine (G), and Thymine (T). In ribonucleic acid (RNA), Thymine is replaced by Uracil (U) and the reference genome data 102 would be included of symbols A, C, G, and U. An example portion of the reference genome data 102 includes nucleotides GAGTGAA and TTGA, shown in item 101.

The genomic data referred to in the present disclosure can include, for example, and not as a limitation, nucleotide sequences, Deoxyribonucleic acid (DNA) sequences, or Ribonucleic acid (RNA). In some implementations, a reference sequence includes a synthetic sequence conceived, at least in part, to improve the compressibility of the reads in view of further processing.

The computer 104 provides the reference genome data 102 to the k-mer engine 106. The k-mer engine 106 generates one or more k-mers based on the obtained reference genome data 102. For example, the k-mer engine 106 can use a moving window to extract portions of the reference genome data 102. The moving window can have a length indicating the number of nucleotides extracted from the reference genome data 102 into a given k-mer. The moving window can be of a fixed or variable width producing k-mers of a fixed or variable length. The moving window can start at a beginning of the reference genome data 102 and move to an end of the reference genome data 102.

In some implementations, the k-mer engine 106 extracts a k-mer at regular intervals. For example, the k-mer engine 106 can use a moving window starting at a first position in the reference genome data 102 to obtain a first k-mer. The k-mer engine 106 can move the window by an interval, such as one or more nucleotides in the reference genome data 102, to a second position in the reference genome data 102 to obtain a second k-mer representing that second position.

Within this specification, a given k-mer is defined as a sequence of sequential nucleotides of a genomic sequence where the number of nucleotides in the genomic sequence for a given k-mer is defined by "k" and the nucleotides of the genomic sequence are represented by strings of As, Cs, Gs, and Ts for DNA sequences or As, Cs, Gs, and Us for RNA sequences. The nucleotides may represent a nucleotide of a references sequence or a base call generated by a nucleic acid sequencer that corresponds to a nucleotide of a sample sequence.

The k-mer engine 106 generates k-mers 102a-d from the reference genome data 102. Each of the k-mers 102a-d represent a portion of the reference genome data 102. For example, each of the k-mers 102a-d correspond to a particular subset sequence present in the reference genome data 102 having a nucleotide length of k, where k is any positive integer greater than 0. For example, a k-mer of the k-mers 102a-d can represent a nucleotide sequence of length k nucleotides including nucleotides "AAGTAT". The genomic data 102 can include at least one instance of the sequence "AAGTAT". In some implementations, the k-mer engine 106 generates k-mers that are 22 nucleotides long. In some implementations, the k-mer engine 106 generates k-mers that are 16 nucleotides long. In general, longer k-mers with more nucleotides occur less frequently in genomic sequences making the positions more unique. More unique positions increases the likelihood that a determined candidate alignment location is accurate.

Selection of a particular k-mer seed length can be made on an implementation-by-implementation basis based on the technical improvements sought by the particular implementation. For example, selection of a k-mer size of 22 nucleotides can result in a hash table that is larger in size than a hash table generated using a selected k-mer size of 16 nucleotides, but may result in faster candidate alignment determinations in a manner that is more accurate. Alternatively, selection of k-mer size of 16 can result in a hash table that is smaller in size than a hash table generated using a selected k-mer size of 22 nucleotides, but may result in slower candidate alignment determinations in a manner that is less accurate. Any even number of nucleotides between 16 and 22, less than 16, or greater than 22 can also be selected and be used to achieve similar technological benefits and/or tradeoffs.

The k-mer engine 106 provides the k-mers 102a-d to the filter engine 108. The filter engine 108 includes a filter hash engine 110 and abundance filtering engine 114. In some implementations, the filter hash engine 110 of the filter engine 108 generates a hash value for each of the k-mers 102a-d. For example, the filter hash engine 110 can include one or more hash functions. The filter hash engine 110 can apply the one or more hash functions to each k-mer of the k-mers 102a-d. Based on applying the one or more hash functions to each k-mer, the filter hash engine 110 can generate a hash value for each k-mer.

In some implementations, the filter hash engine 110 uses the generated hash values 112 to filter one or more k-mers. For example, the filter hash engine 110 can perform one or more modulo operations. The filter hash engine 110 can obtain a modulo value determined by a user or automated process. The filter hash engine 110 can perform one or more modulo operations with the obtained modulo value. In some implementations, the filter hash engine 110 generates a result from a modulo operation and uses the result to determine whether to filter a given k-mer. For example, the filter hash engine 110 can perform one or more modulo operations on the hash value generated for k-mer 102a. The filter hash engine 110 can obtain a result from the one or more modulo operations and compare the result to predetermined criteria. Based on comparing the result to the predetermined criteria, the filter hash engine 110 can determine whether to filter out a corresponding k-mer or not.

In some implementations, predetermined criteria includes one or more values of a modulo operation result. For example, the filter hash engine 110 can generate a result from a modulo operation on a hash value of a k-mer of the k-mers 102a-d and compare the result to one or more values. The one or more values can include the value 0. The filter hash engine 110 can compare the result to 0 and filter the corresponding k-mer based on whether or not the result matches one or more of the values. In some implementations, results that match the one or more values are filtered. In some implementations, results that do not match the one or more values are filtered.

In the example of FIG. 1, the filter hash engine 110 filters out k-mer 102b based on the generated hash of the hash values 112 and one or more modulo operations. The filter hash engine 110 retains k-mers 102a and 102c-d.

The filter engine 108 performs abundance filtering engine 114. In some implementations, the filter engine 108 provides the filtered k-mer set obtained from the filter hash engine 110 to the abundance filtering engine 114. In this way, the filter engine 108 can more efficiently determine occurrences by only determining occurrences for the remaining k-mers after the filtering of the filter hash engine 110.

In some implementations, the abundance filtering engine 114 includes generating a number of occurrences 116 for each k-mer 102a-d. In some implementations, the abundance filtering engine 114 includes generating a number of occurrences 116 for each of the filtered k-mers, such as k-mers 102a and 102c-d. For example, the filter engine 108 can compare the nucleotide sequence of each k-mer to sequences in the reference genome data 102. The filter engine 108 can increment an occurrence counter for a given k-mer based on a number of sequences in the reference genome data 102 matching the given k-mer. For example, the filter engine 108 can compare a first nucleotide representation of the k-mer 102a with a first nucleotide of the reference genome data 102. The filter engine 108 can compare a second nucleotide representation of the k-mer 102a with a second nucleotide of the reference genome data 102. If one or more representations of the k-mer 102a match a sequence of the reference genome data 102, the filter engine 108 can increment an occurrence counter for the k-mer 102a.

In some implementations, the filter engine 108 filters one or more k-mers based on a number of times a k-mer occurs in a corresponding reference sequence. For example, the filter engine 108 can generate occurrences 116. The filter engine 108 can compare each occurrence value of the values 116 to a threshold value. Based on the comparison, the filter engine 108 can filter one or more k-mers. For example, the filter engine 108 can filter out k-mers that occur more than, or equal to, a certain number of times within a reference sequence, such as the reference genome data 102. In this way, the filter engine 108 can identify a set of k-mers that is more unique, in that they appear less often in a corresponding reference sequence, than another set with higher numbers of occurrences. In some implementations, k-mers that occur less often in a reference sequence are more indicative of accurate candidate alignments because there are fewer false positives. The k-mers can improve the efficiency of subsequent candidate alignment determination.

The filter engine 108 compares the number of occurrences of the k-mer 102c with a threshold and, based on the comparison, filters out the k-mer 102c. In some implementations, a threshold occurrence value is used. For example, the filter engine 108 can determine to filter out a k-mer if it occurs more than a number of times, e.g., 20, within the reference genome data 102.

The filter engine 108 generates index data 118 and 120 for the filtered set of k-mers 102a and 102d. The index data 118 and 120 includes a location of one or more occurrences enumerated in occurrence values 116 and data representing the k-mers 102a and 102d. The index data 118 includes the reference location 128 indicating one or more occurrences of the sequence corresponding to k-mer 102a in the reference genome data 102. The index data 120 includes the reference location 130 indicating one or more occurrences of the sequence corresponding to k-mer 102d in the reference genome data 102. In some implementations, the index data 118 and 120 include only the first occurrence, among one or more possible occurrences in a reference sequence, of a k-mer.

The filter engine 108 provides the index data 118 and 120 to the hash table engine 122. The hash table engine 122 obtains the index data 118 and 120 and generates hash values for the k-mers 102a and 102d corresponding to the index data 118 and 120. In some implementations, the hash table engine 122 generates hash table 132. For example, the hash table engine 122 can generate one or more hash values and store them in memory of the computer 104 or a device communicably connected to the computer 104.

The hash table engine 122 generates one or more hash values for each of the filtered k-mers 102a and 102d. In some implementations, the hash table engine 122 generates a hash signature using a hash signature function 124 and a hash table value using a hash table value function 126. For example, the hash table engine 122 can obtain the data representing the sequences of k-mers 102a and 102d. The hash table engine 122 can apply both the hash signature function 124 and the hash table value function 126 to the sequences of k-mers 102a and 102d.

In some implementations, a signature generated from the hash signature function 124 is used as a key in the hash table 132. For example, the hash table engine 122 can generate a signature value for the k-mer 102a based on the index data 118. The hash table engine 122 can use the hash signature function 124 to generate the signature value based on the k-mer 102a. In some implementations, the signature generated by the hash table engine 122 is a compressed version of the k-mer 102a. For example, the k-mer 102a can be represented, as a sequence of nucleotides, in 16 bits for a k=16 k-mer with 16 nucleotides. The signature generated by the hash table engine 122 and the hash signature function 124 can be represented by 8 bits. This key compression significantly reduces the required size of the hash table 132. The decreased size increases look up time, storage time, and overall performance.

In some implementations, the hash table engine 122 generates a hash table item for each of the filtered k-mers 102a and 102d to be stored in the hash table 132. For example, the hash table engine 122 can generate a hash table value using the hash table value function 126 applied to each of the k-mers 102a and 102d to generate a hash table value for storing data corresponding to the k-mers 102a and 102d in the hash table 132. In some implementations, a hash table value represents an index in the hash table 132. The hash table engine 122 can store data corresponding to the given k-mer, such as a signature of a k-mer generated by the hash signature function 124, as well as one or more locations of the k-mer occurrence within a genomic read, such as the reference genome data 102.

The hash table engine 122 stores the reference locations 128 and 130 in the hash table 132. In some implementations, the hash table engine 122 stores the reference locations 128 and 130 as the value within a hash table item for each of the filtered k-mers 102a and 102d. For example, the hash table engine 122 can generate a hash table item that includes a location, such as reference locations 128 and 130, with a key generated by the hash signature function 124, at an index of the hash table 132 generated by the hash table value function 126.

The hash table engine 122 provides data corresponding to the hash table 132 to the hash storage 134. In some implementations, the hash table engine 122 sends data for each of the index data 118 and 120 to the hash storage 134. In some implementations, the hash table engine 122 sends data for one or more other entries of the hash table 132. In some implementations, the hash storage 134 includes memory storage on the computer 104. In some implementations, the hash storage 134 includes memory storage of a device communicably connected to the computer 104.

Figure 2:
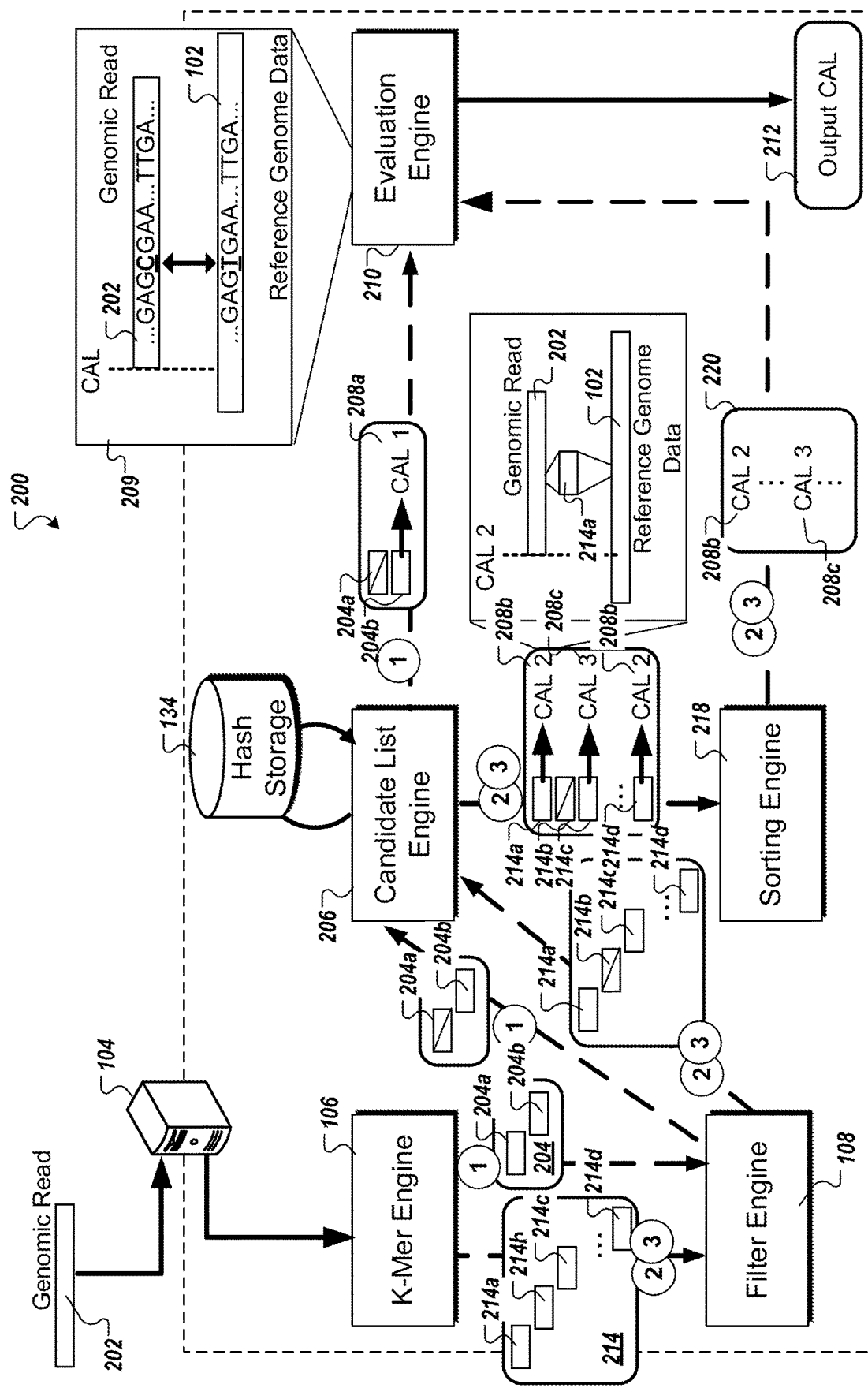
FIG. 2 is a diagram showing an example of a system for performing software-accelerated genomic mapping operations using the hash table generated using the system of FIG. 1 to select a candidate alignment location of a genomic read.

FIG. 2 is a diagram showing an example of a system 200 for performing software-accelerated genomic mapping operations using the hash table generated using the system of FIG. 1 to select a candidate alignment location of a genomic read. The system 200 includes the computer 104, the k-mer engine 106, the filter engine 108, the candidate list engine 206, the hash storage 134, the sorting engine 218, and the evaluation engine 210.

In some implementations, the computer 104 operates in multiple stages. For example, a first stage can include generating one or more k-mers, generating one or more candidate alignments based on the one or more k-mers, and evaluating the candidate alignments. Second and third stages can include generating one or more k-mers, generating one or more candidate alignments based on the one or more k-mers, sorting the list of one or more candidate alignments, and evaluating the candidate alignments in the order of the sorted list. In the example of FIG. 1, the first stage is shown as path 1. The second stage is shown as path 2. The third stage is shown as path 3.

The computer 104 obtains genomic read data 202. The genomic read data 202 can include a sequence of base calls generated by a nucleic acid sequencing device by sequencing a biological sample obtained from an organism. The organism can include a human, an animal, an insect, a reptile, a plant, or any other organism. Each base call of the read can correspond to a nucleotide and be represented by an A, C, T, or G. In the case of an RNA sequence read, each base call of the read can correspond to a nucleotide that is represented by an A, C, G, or U. The computer 104 can be used to determine the alignment between the genomic read data 202 and the reference genome data 102. Once properly aligned to the reference genome, variants between the genomic read data 202 and the reference genome data 102 can be analyzed in order to infer a number of conclusions about the organism from which the genomic read data 202 was sequenced. These conclusions can include, e.g., types of treatment that may be best suited for the organism for one or more particular ailments.

The computer 104 provides the genomic read data 202 to the k-mer engine 106. As discussed in reference to FIG. 1, the k-mer engine 106 obtains one or more k-mers based on the obtained genomic read data 202 in the same manner described with reference to obtaining k-mers from a reference genome 102, described above. In the first stage, the k-mer engine 106 generates k-mers 204 including k-mers 204a and 204b. The first k-mer that is not filtered out can be evaluated to determine if a corresponding candidate alignment satisfies one or more criteria. In some implementations, the k-mer engine 106 generates a single k-mer. For example, the filter engine 108 can determine that the first k-mer obtained by the k-mer engine 106 from the genomic read data 202 satisfies one or more filter criteria, such as hash filtering or abundance filtering. The filter engine 108 can then send data corresponding to that single k-mer to the candidate list engine 206.

In some implementations, the computer 104 filters k-mers before hash table look up. For example, the computer 104 can use the same filtering techniques used on the k-mers 102a-d to generate a portion of the hash table 132. In some implementations, applying the filter before hash table look up increases efficiency and reduces runtime relative to conventional processes. For example, the hash table 132 is generated based on k-mers that were filtered according to a particular filter method, such as filters applied by the filter engine 108. Newly generated k-mers, such as the k-mers 204, can be generated in order to find matching k-mers in the hash table 132. By using the same filtering method on the k-mers used to generate the hash table 132 and the k-mers used to look up k-mers in the hash table 132, the computer 104 prevents newly generated k-mers that are definitely not in the hash table 132 from being used to query the hash storage 134. For example, without applying the same filter processes, a k-mer that was filtered out during the generation of the hash table 132 may not be filtered out during a candidate alignment determination stage, such as the first processing stage of FIG. 2. A resulting query on that k-mer would waste processing resources and increase runtime.

In the example of FIG. 2, the filter engine 108 filters out k-mer 204a and retains k-mer 204b. The filter engine 108 can use one or more filtering techniques, including the filtering techniques described in reference to FIG. 1, to filter k-mers generated by the k-mer engine 106 from the genomic read data 202.

In some implementations, the filter engine 108 uses particular parameters to filter the k-mers based on the stage of processing. For example, in the first stage of processing, the filter engine 108 can use a first modulo value to perform one or more modulo operations. In a second stage of processing, the filter engine 108 can use a second modulo value to perform one or more modulo operations. In subsequent stages, the filter engine 108 can use different modulo values. As discussed in FIG. 1, the modulo value and modulo operations can be used to filter one or more k-mers. In general, the filter engine 108 can adjust filter parameters to increase a number of selected k-mers over time. In this way, stages with fewer k-mers are processed before stages with more k-mers to increase efficiency and decrease run time of the system.

In some implementations, the filter engine 108 decreases a modulo value and maintains or increases one or more result values indicating not to filter a k-mer. For example, a modulo value for a first stage of processing can be 32. As discussed in FIG. 1, the filter engine 108 can apply a modulo function to a hash generated based on a k-mer. An example expression to generate a result can include: generated_hash mod 32. In some implementations, if the result is 0, the k-mer is further processed and if the result is not 0, the k-mer is not further processed. In this case, 0 is a result value indicating not to filter a k-mer.

In some implementations, the filter engine 108 increases the number of k-mers to process by increasing the number of result values indicating not to filter a k-mer. For example, the filter engine 108 can not filter, and further process a given k-mer, if a corresponding hash value modulo a given modulo value, is equal to 0 or 1, greater than 3, less than 5, among others.

The filter engine 108 can increase the number of k-mers to process by decreasing the modulo value and maintaining one or more result values indicating not to filter a k-mer. For example, the filter engine 108 can not filter, and further process a given k-mer, if a corresponding hash value modulo a first modulo value, is equal to 0 or other value. In this way, the filter engine 108 selects one out of the number corresponding to the first modulo value. If the first modulo value is 32, the filter engine 108 will, on average, select one out of every 32 k-mers generated by the k-mer engine 106. To increase the number of k-mers to process, such as in a later stage of processing, the filter engine 108 can decrease the first modulo value to a second modulo value.

The filter engine 108 sends the k-mer 204b to the candidate list engine 206. In some implementations, the filter engine 108 does not send the k-mer 204a. The candidate list engine 206 queries the hash storage 134 based on the k-mer 204b. In some implementations, the candidate list engine 206 hashes the k-mer 204b to generate a hash value. The hash value can be used as a query key to search the hash table 132 stored on the hash storage 134.

As discussed in FIG. 1, the hash storage 134 stores indexes and reference locations for one or more k-mers extracted from the reference genome data 102 in the hash table 132. If the k-mer 204b is present within the hash table 132, the candidate list engine can obtain a corresponding reference location. In some implementations, the key in the hash table is a hash of the k-mer of the reference genome. By using the same hash function as was used to generate the keys of the hash table 132, the candidate list engine 206 can generate keys for new k-mers that, if matching keys of the hash table 132, indicate that the k-mer was present in the reference genome data 102 and the hash table 132 includes a location of the k-mer within the reference genome data 102.

In some implementations, the candidate list engine 206 queries the hash storage 134 based on the k-mer 204b and obtains a reference location of a corresponding k-mer in the reference genome data 102. By comparing the location of the k-mer 204b within the genomic read data 202 and the reference location of a corresponding k-mer in the reference genome data 102, the candidate list engine 206 can generate a candidate alignment location. The candidate alignment condition can indicate a position within the reference genome data 102 where the genomic read data 202 aligns.

In some implementations, the candidate list engine 206 provides a first candidate alignment location 208a corresponding to the k-mer 204b, to the evaluation engine 210. The evaluation engine 210 obtains data of the reference genome data 102 and data of the genomic read data 202. The evaluation engine 210 compares one or more nucleotides of the reference genome data 102 and data of the genomic read data 202. In some implementations, the evaluation engine 210 starts with a first nucleotide of the reference genome data 102 and data of the genomic read data 202 at the first candidate alignment location. If the nucleotides do not match, the evaluation engine 210 can increment a mismatch counter. The evaluation engine 210 can evaluate all nucleotides in a portion of the genomic read data 202 or stop after a number of mismatches are counted. In some implementations, the evaluation engine 210 evaluates each and every nucleotide in the genomic read data 202.

In some implementations, the evaluation engine 210 generates an evaluation result based on the first candidate alignment location 208a. For example, the evaluation engine 210 can generate a value indicating a number of one or more mismatches between the genomic read data 202 and the reference genome data 102 at the first candidate alignment location 208a. Each mismatch can indicate a nucleotide of the genomic read data 202 at a position relative to the first candidate alignment location 208a being different than a corresponding nucleotide of the reference genome data 102 at the same position relative to the first candidate alignment location 208a (e.g., FIG. 2 shows a comparison graphically in item 209 where the nucleotide "C" of the genomic read data 202 is different than the nucleotide "T" in the reference genome data 102 at the same position relative to the candidate alignment location (CAL)).

In some implementations, the computer 104 compares evaluation results of the evaluation engine 210 to a threshold. For example, the computer 104 can compare the number of mismatches to a mismatch threshold. If the number of mismatches satisfies the threshold, such as being less or equal to the threshold or less than the threshold, among others, the computer 104 can stop processing and select the first candidate alignment location 208a as the actual alignment of the genomic read data 202. If the number of mismatches does not satisfy the threshold, the computer 104 can execute additional processing stages. The computer 104 can generate and provide a notification to a device of a user or a display of the computer 104. The notification can include information indicating that the first processing and evaluation stage did not result in an alignment that satisfied criteria, such as a threshold. The computer 104 can obtain and include details of the alignment, filtered k-mers, evaluation results, among others, in the notification.

In some implementations, the computer 104 executes one or more processing stages after a first stage. For example, the computer 104 can determine that the first candidate alignment location 208a does not satisfy a threshold. The computer 104 can determine that there are no matching k-mers from the reference genome data 102 in the hash storage 134. In response to one or more of these determinations, the computer 104 can execute subsequent processing stages.

In some implementations, the computer 104 executes a second processing stage. For example, after a first processing stage does not produce an alignment that satisfies criteria, the k-mer engine 106 can provide additional k-mers 214 to the filtering engine 108 to determine a new set of filtered k-mers to process. In some implementations, the filter engine 108 filters the k-mers 214 using a set of filtering parameters different from filtering parameters used in the first processing stage. For example, the filter engine 108 can adjust filtering parameters, such as resulting values to include in further processing, and modulo values to increase or decrease the number of k-mers used in subsequent processing.

In some implementations, the filter engine 108 provides the filtered k-mers 214a and 214c-d to the candidate list engine 206. The filter engine 108 can filter out the k-mer 214b using one or more filtering techniques as described herein. The candidate list engine 206 can query the hash storage 134 to obtain a reference location for each k-mer of the filtered k-mers 214a and 214c-d. In some implementations, the candidate list engine 206 queries the hash storage 134 using one or more hashes representing each of the filtered k-mers 214a and 214c-d. For example, the candidate list engine 206 can generate a hash value by applying a hash function to each of the filtered k-mers 214a and 214c-d to generate a hash function result. The candidate list engine 206 can query the hash storage 134 to find hash table items with a key that matches the hash function results. Matching keys can indicate identical k-mers from the reference genome data 102.

In some implementations, the candidate list engine 206 queries the hash storage 134 based on the filtered k-mers 214a and 214c-d and obtains reference locations for corresponding k-mers in the reference genome data 102. By comparing the location of each k-mer of the filtered k-mers 214a and 214c-d with the obtained reference locations, the candidate list engine 206 can generate a candidate alignment location. The candidate alignment condition can indicate a position within the reference genome data 102 where the genomic read data 202 aligns. The candidate list engine 206 can generate one or more candidate alignment conditions for each of the filtered k-mers 214a and 214c-d.

In some implementations, the candidate list engine 206 generates one or more candidate alignment locations. For example, the candidate list engine 206 can generate a second candidate alignment location 208b and a third candidate alignment location 208c. K-mers used to generate alignments are referred to as supporting the alignment. One or more k-mers of the filtered k-mers 214a and 214c-d can support the same candidate alignment location. For example, both the k-mer 214a and the k-mer 214d support the second candidate alignment location 208b. The k-mer 214c supports the third candidate alignment location 208c.

In some implementations, the candidate list engine 206 provides a list of one or more candidate alignment locations to the sorting engine 218. The sorting engine 218 can obtain the candidate alignment locations and sort the candidate alignment locations. In some implementations, the sorting engine 218 sorts candidate alignment locations based on the number of supporting k-mers. For example, because both k-mers 214a and 214d support the second candidate alignment location 208b and only the k-mer 214c supports the third candidate alignment location 208c, more k-mers support the second candidate alignment location 208b compared to the third candidate alignment location 208c. Because more k-mers support the second candidate alignment location 208b compared to the third candidate alignment location 208c, the sorting engine 218 can sort the second candidate alignment location 208b above the third candidate alignment location 208c.

In some implementations, the sorting engine 218 provides a sorted list 220 to the evaluation engine 210. For example, the sorting engine 218 can generate the sorted list 220 including the second candidate alignment location 208b sorted before the third candidate alignment location 208c. The sorted list 220 can be stored in any suitable data format including a linked list, array, queue, or the like.

In some implementations, the evaluation engine 210 obtains data from the sorting engine 218. For example, the sorting engine 218 can provide the sorted list 220 to the evaluation engine 210. The evaluation engine 210 can evaluate each item of the sorted list 220 in the order of the sorted list 220. For example, the evaluation engine 210 can evaluate the second candidate alignment location 208b prior to evaluating the third candidate alignment location 208c. The computer 104 can compare the evaluation results for each item of the sorted list 220 to an evaluation threshold to determine whether to select the alignment as the actual alignment. If the alignment satisfies the evaluation threshold, the computer 104 can prevent further processing by the evaluation engine 210 and output the alignment location as an output candidate alignment location 212.

In some implementations, the computer 104 adjusts an evaluation threshold based on a processing stage. For example, for a first processing stage, the computer 104 can require a lower number of mismatches for a selected actual alignment compared to a later processing stage. For a processing stage after the later processing stage, the number of mismatches can be maintained, increased, or decreased.

In some implementations, the computer 104 selects the alignment of the first processing stage only if the alignment results in 0 mismatches. In some implementations, the computer 104 compares an evaluation result to a threshold number of mismatches, e.g., 8, and based on the evaluation result satisfying the number of mismatches, e.g., less than or equal to, or less than, the threshold, the computer 104 selects the corresponding alignment location as the output candidate alignment location 212. In some implementations, the evaluation engine 210 stops during a processing stage and outputs the last processed alignment if the alignment satisfies a mismatch threshold. For example, the mismatch threshold for the first processing stage can be 0 requiring the evaluation of the first candidate alignment location 208a to have no mismatches. The mismatch threshold for the second processing stage can be 8, requiring the evaluation of the second candidate alignment location 208b or the third candidate alignment location 208c to have less than, or less than or equal to, 8 mismatches. The mismatch threshold for the third processing stage can be 4, requiring the evaluation of a subsequent candidate alignment location to have less than, or less than or equal to, 4 mismatches.

In some implementations, the evaluation engine 210 generates evaluation results for each candidate alignment of the sorted list 220. In some implementations, none of the evaluation results for each candidate alignment of the sorted list 220 satisfies a predetermined criteria, such as a mismatch threshold. In this case, the computer 104 can start a third processing stage by generating a new set of k-mers and processing the k-mers as shown for the k-mer set 214 and filtered k-mers 214a and 214c-d.

In some implementations, the k-mer engine 106 and the filter engine 108 generate k-mers for the third processing stage similar to the k-mers 214 according to one or more parameters. For example, the k-mer engine 106 can extract k-mers from the genomic read data 202 of a size "k" corresponding to a seed length parameter. The filter engine 108 can filter the extracted k-mers according to one or more filter parameters. For example, the filter engine 108 can use one or more filtering techniques, such as hash filtering or abundance filtering. In some implementations, the modulo value used to generate results of modulo operations changes in the third processing stage compared to the second processing stage. For example, the modulo value can decrease from 32 to 8. The filtering engine can effectively decrease filtering by selecting one out of every 32 k-mers in the second processing stage and selecting one out of every 8 k-mers in the third processing stage. In general, the parameters to generate k-mers in subsequent processing stages can be adjusted by the user or automated process based on the results of the processed k-mers in one or more prior processing stages.

In some implementations, the computer 104 generates a filtered set of k-mers in a third processing stage after a first and second processing stage fail to select an alignment that satisfies conditions. The filtered set of k-mers can be used to generate a candidate alignment list by the candidate list engine 206 in the same way as the filtered k-mers 214a and 214c-d. The alignment list can be sorted and evaluated in the same way as the sorted list 220.

Based on one or more of the processing stages 1 through 3, the computer 104 selects an alignment location that satisfies an alignment criteria. In some implementations, the alignment criteria includes a mismatch threshold. The computer 104 can provide the alignment location as the output candidate alignment location 212. The computer 104 can provide data indicating the output candidate alignment location 212 to a memory storage device, a display, a device of a user, another communicably connected device, among others.

In some implementations, a first computer performs one or more operations performed by the computer 104 as discussed in FIG. 1 and a second computer performs one or more operations performed by the computer 104 as discussed in FIG. 2. For example, at least two distinct computer devices can perform one or more operations performed by the computer 104. In some implementations, a first computer performs hash table generation including performing one or more operations discussed in reference to FIG. 1. In some implementations, a second computer, distinct from the first computer, performs genomic mapping including performing one or more operations discussed in reference to FIG. 2.

Figure 3:
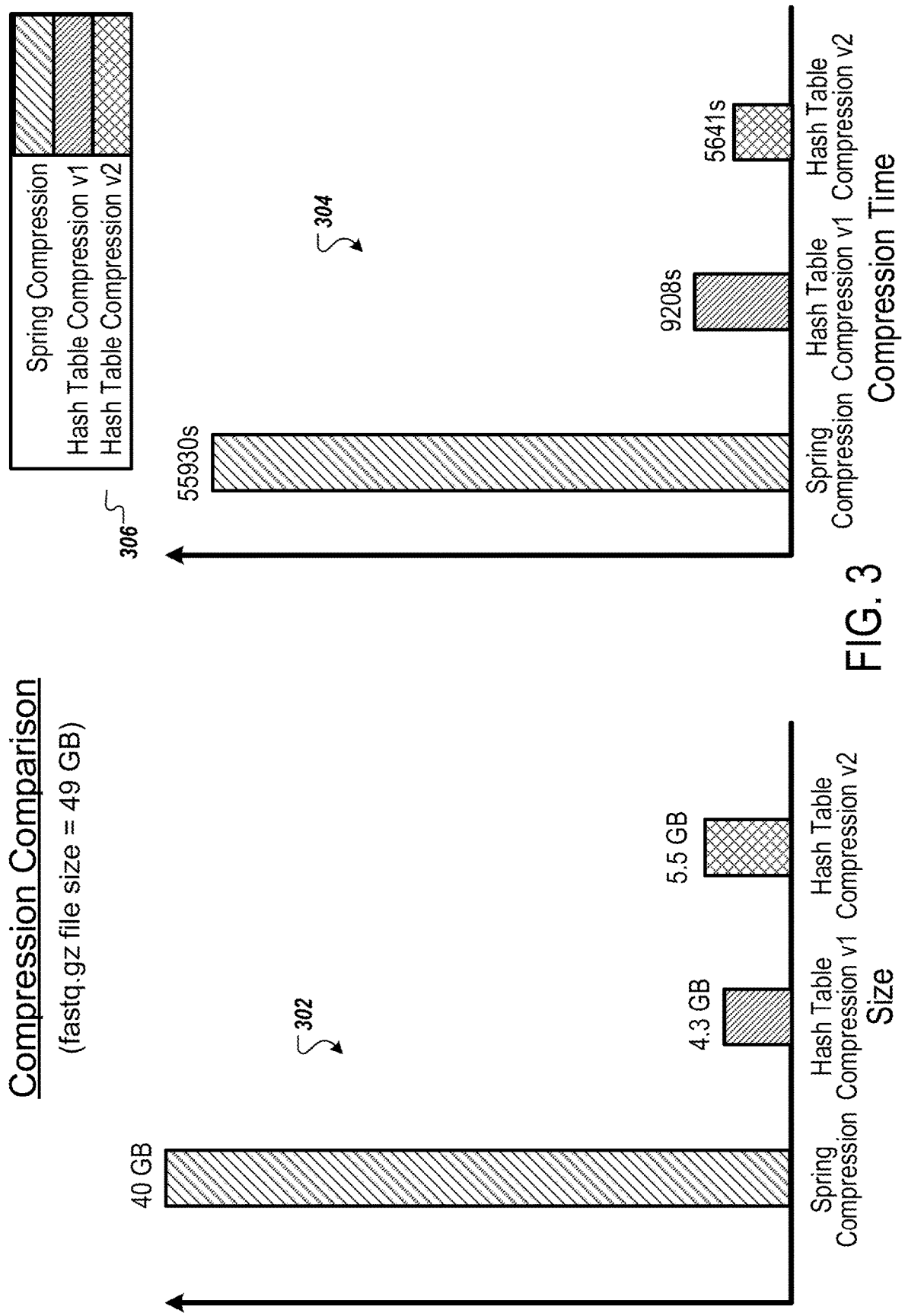
FIG. 3 is a graphical depiction of experimental results comparing data compression methods for genomic data.

FIG. 3 is a graphical depiction of experimental results comparing data compression methods for genomic data. FIG. 3 shows a comparison between a spring compression method and two versions that use a hash table compression method. The spring compression method is a compression method available on GitHub. The spring compression method is a compression tool for FASTQ files containing up to 4.29 Billion reads. Key 306 shows the graphical representation for each of the three methods.

In some implementations, a FASTQ file is a text file that includes the sequence data from the clusters that pass filter on a flow cell. If samples were multiplexed, the first step in FASTQ file generation is demultiplexing. Demultiplexing assigns clusters to a sample, based on the cluster's index sequence(s). After demultiplexing, the assembled sequences are written to FASTQ files per sample. If samples were not multiplexed, the demultiplexing step does not occur, and, for each flow cell lane, all clusters are assigned to a single sample.

In some implementations, for a single-read run, one Read 1 (R1) FASTQ file is created for each sample per flow cell lane. For a paired-end run, one R1 and one Read 2 (R2) FASTQ file is created for each sample for each lane. FASTQ files are compressed and created with the extension *.fastq.gz.

In some implementations, for each cluster that passes filter, a single sequence is written to the corresponding sample's R1 FASTQ file, and, for a paired-end run, a single sequence is also written to the sample's R2 FASTQ file. In some implementations, each entry in a FASTQ files includes 4 lines: (i) a sequence identifier with information about the sequencing run and the cluster (the exact contents of this line vary by based on conversion software used), (ii) the sequence (e.g., the base calls; A, C, T, G and N), (iii) a separator (e.g., a plus (+) sign), and (iv) the base call quality scores (e.g., Phred+33 encoded, using ASCII characters to represent the numerical quality scores).

FIG. 3 shows results from the compression of a 49 GB fastq.gz data file. Chart 302 shows a comparison of final compressed size generated by each of the spring compression, hash table compression v1, and hash table compression v2. The spring compression generates a compressed version of the 49 GB fastq.gz data file that is 40 GB. The hash table compression v1 generates a compressed version of the 49 GB fastq.gz data file that is 4.3 GB. The hash table compression v2 generates a compressed version of the 49 GB fastq.gz data file that is 5.5 GB.

The hash table compression v2 includes the method of compression described herein, e.g., FIG. 1 and corresponding description. The hash table compression v1 is a similar method that also uses a hash table but with different parameters. For example, v1 includes a seed length parameter of 16. V2 includes a seed length parameter of 22. V2, and the increase in seed length, allows v2 to have more seeds in the reference genome with unique positions than v1 and increases the number of total distinct seeds. The trade-off is that this implementation of v2 requires more memory usage than v1.

In some implementations, the hash table compression v1 with a seed length of 16 extracts one or more seeds from a reference genome 16 nucleotides in length. In some implementations, v1 inserts $143 \times 10^6$ k-mers into the hash table. The hash table can have $2^{28}$ cells (e.g., 5B per cell), resulting in load factor of 0.53 and total hash size of $2^{28} \times 5B = 1280$ MB.

In some implementations, the hash table compression v2 with a seed length of 22 extracts one or more seeds from a reference genome 22 nucleotides in length. In some implementations, v2 inserts $299 \times 10^6$ k-mers into the hash table. The hash table can have $2^{29}$ cells (e.g., 5B per cell) resulting in load factor of 0.55 and a total hash size of $2^{28} \times 5B = 2560$ MB.

The increased memory usage is shown in FIG. 3 where the hash table compression v2 generates a compressed version of the 49 GB fastq.gz file that is 5.5 GB while the hash table compression v1 generates a compressed version of the 49 GB fastq.gz file that is 4.3 GB.

However, the hash table compression v2 results in faster compression as shown in chart 304. Both the hash table compression v1 and the hash table compression v2 are quicker than the spring compression method (e.g., 55930 seconds). The hash table compression v2 is quicker than the hash table compression v1 (e.g., 5641 seconds compared to 9208 seconds).

In some implementations, increases in efficiency are achieved by the hash table compression v2 because of the mapping engine's process of generating the input to the compression algorithm. For example, the computer 104 can generate mapped reads faster and with a tailored level of accuracy for compression algorithms that results in better compression performance over prior methods, such as hash table compression v1 and spring compression.

Figure 4:
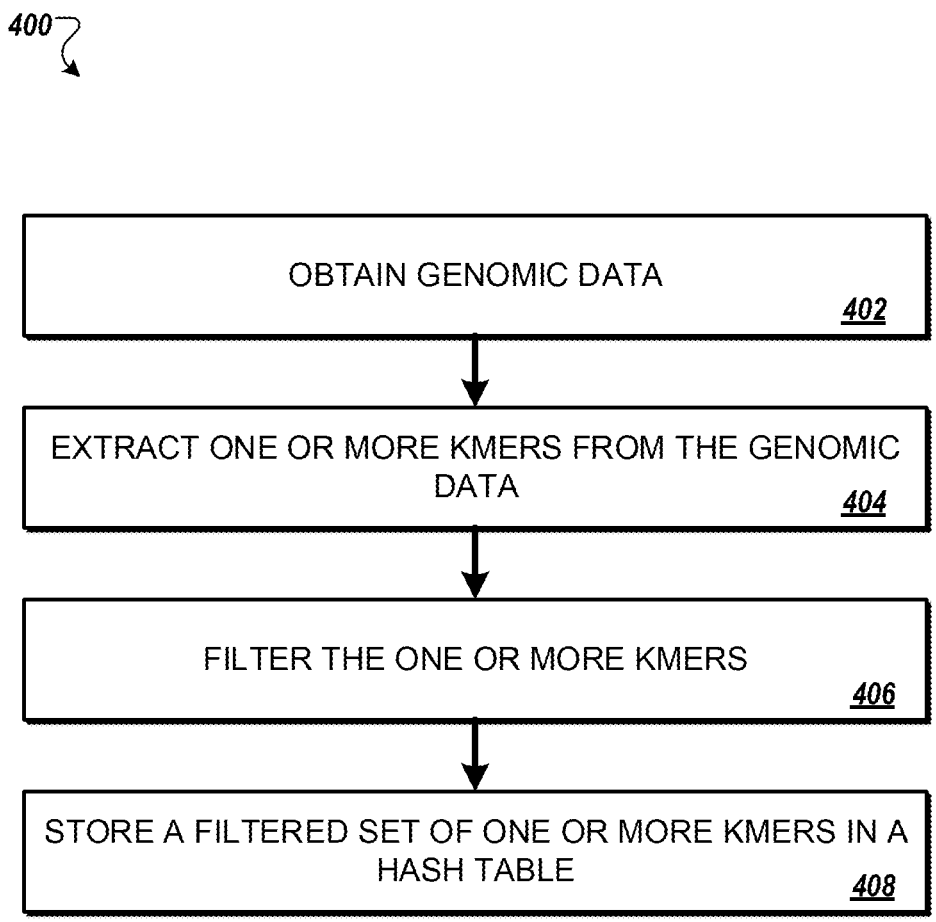
FIG. 4 is a flow diagram illustrating an example of a process for generating a hash table for a multi-pass software accelerated genomic read mapping engine.

FIG. 4 is a flow diagram illustrating an example of a process 300 for generating a hash table for a multi-pass software accelerated genomic read mapping engine. The process 400 may be performed by one or more electronic systems, for example, the computer 104 of system 100 in FIG. 1.

The process 300 includes obtaining genomic data (402). For example, the computer 104 can obtain the reference genome data 102. The reference genome data 102 can include symbols A, C, G, and T representing four types of nucleotides present in deoxyribonucleic acid (DNA), namely Adenine (A), Cytosine (C), Guanine (G), and Thymine (T). In ribonucleic acid (RNA), Thymine is replaced by Uracil (U) and the reference genome data 102 would be included of symbols A, C, G, and U.

The process 300 includes extracting one or more k-mers from the genomic data (404). For example, the k-mer engine 106 can obtain one or more extraction parameters from a user or automated process. The parameters can include a seed length indicating the length of seeds to extract into extracted k-mers. The k-mer engine 106 can generate one or more k-mers from the reference genome data 102.

The process 300 includes filtering the one or more k-mers (406). For example, the filter engine 108 can perform one or more filtering methods on the extracted k-mers to generate a subset of k-mers for inclusion in the hash table 132. In some implementations, the filter engine 108 includes a filter hash engine 110 and an abundance filtering engine 114.

The process 300 includes storing a filtered set of one or more k-mers in a hash table (408). For example, the hash table engine 122 can generate a hash table based on one or more of the filtered k-mers generated by the filter engine 108. The hash table engine 122, or other component of the computer 104 or connected computer or device, can perform hash operations to generate one or more hash function results. The hash function results can be used to store data corresponding to each of the k-mers within the hash table 132. For example, a hash value can be used as a signature in the hash table 132 and a hash value can be used as a hash table index in the hash table 132. In some implementations, the hash values are generated using different hash functions.

Figure 5:
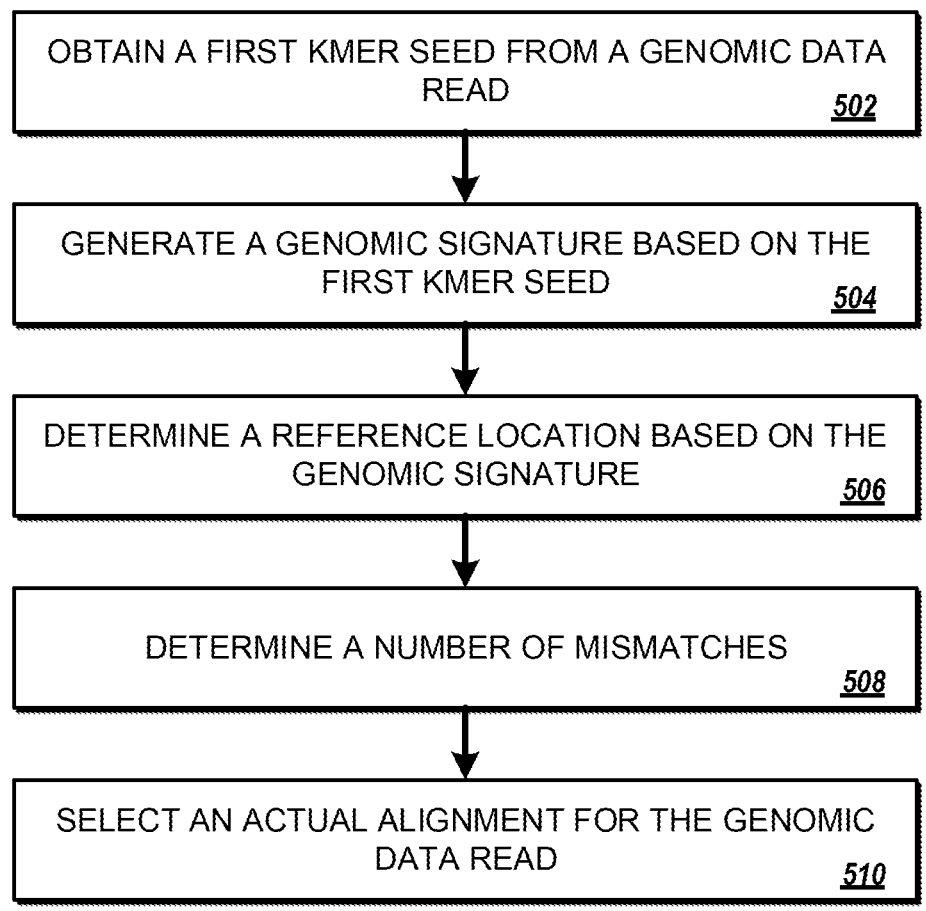
FIG. 5 is a flow diagram illustrating an example of a process for performing software-accelerated genomic mapping operations using the hash table generated using the system of FIG. 1.

FIG. 5 is a flow diagram illustrating an example of a process 500 for performing software-accelerated genomic mapping operations using the hash table generated using the system of FIG. 1. The process 500 may be performed by one or more electronic systems, for example, the computer 104 of system 200 in FIG. 2.

The process 500 includes obtaining a first k-mer seed from a genomic data read (502). For example, the computer 104 can obtain the genomic read data 202. The genomic read data 202 can include a sequence of base calls generated by a nucleic acid sequencing device by sequencing a biological sample obtained from an organism. The organism can include a human, an animal, an insect, a reptile, a plant, or any other organism. Each base call of the read can correspond to a nucleotide and be represented by an A, C, T, or G. In the case of an RNA sequence read, each base call of the read can correspond to a nucleotide that is represented by an A, C, G, or U.

The process 500 includes generating a genomic signature based on the first k-mer seed (504). For example, the candidate list engine 206 can generate a key for a given k-mer based on a hash function used to generate keys for k-mers of genomic reference data. The candidate list engine 206 can query a previously generated hash table storing the genomic reference data, such as the reference genome data 102, using the generated key for the given k-mer. In some implementations, the hash result for the key is generated by applying a hash function to the data representing the given k-mer.

The process 500 includes determining a reference location based on the genomic signature (506). For example, the candidate list engine 206 can query a previously generated hash table storing the genomic reference data, such as the reference genome data 102, using the generated key for the given k-mer. The hash table can store reference locations indicating a position of a stored k-mer within a reference sequence. The candidate list engine 206 can use the location information of the stored k-mer to determine a location of a mapped read, such as the genomic read data 202, in relation to reference genomic data, such as the reference genome data 102.

The process 500 includes determining a number of mismatches (508). For example, the evaluation engine 210 can obtain data of the reference genome data 102 and data of the genomic read data 202. The evaluation engine 210 can compare one or more nucleotides of the reference genome data 102 and data of the genomic read data 202 to determine one or more mismatches based on a starting location determined by the candidate list engine 206.

The process 500 includes selecting an actual alignment for the genomic data read (510). For example, in a first processing stage or pass, the evaluation engine 210 can determine that a number of mismatches satisfies a mismatch threshold and the computer 104 can select the location corresponding to the first generated k-mer seed as the actual alignment for the genomic read data 202. In some implementations, one or more subsequent processing stages are performed based on the evaluation engine 210 generating evaluation results that do not satisfy alignment quality criteria, such as a mismatch threshold. During subsequent processing stages, such as second or third stages, the computer 104 can adjust parameters of the extraction of seeds, hash table look up, evaluation criteria, among others, to select the actual alignment for the genomic read data 202.

Figure 6:
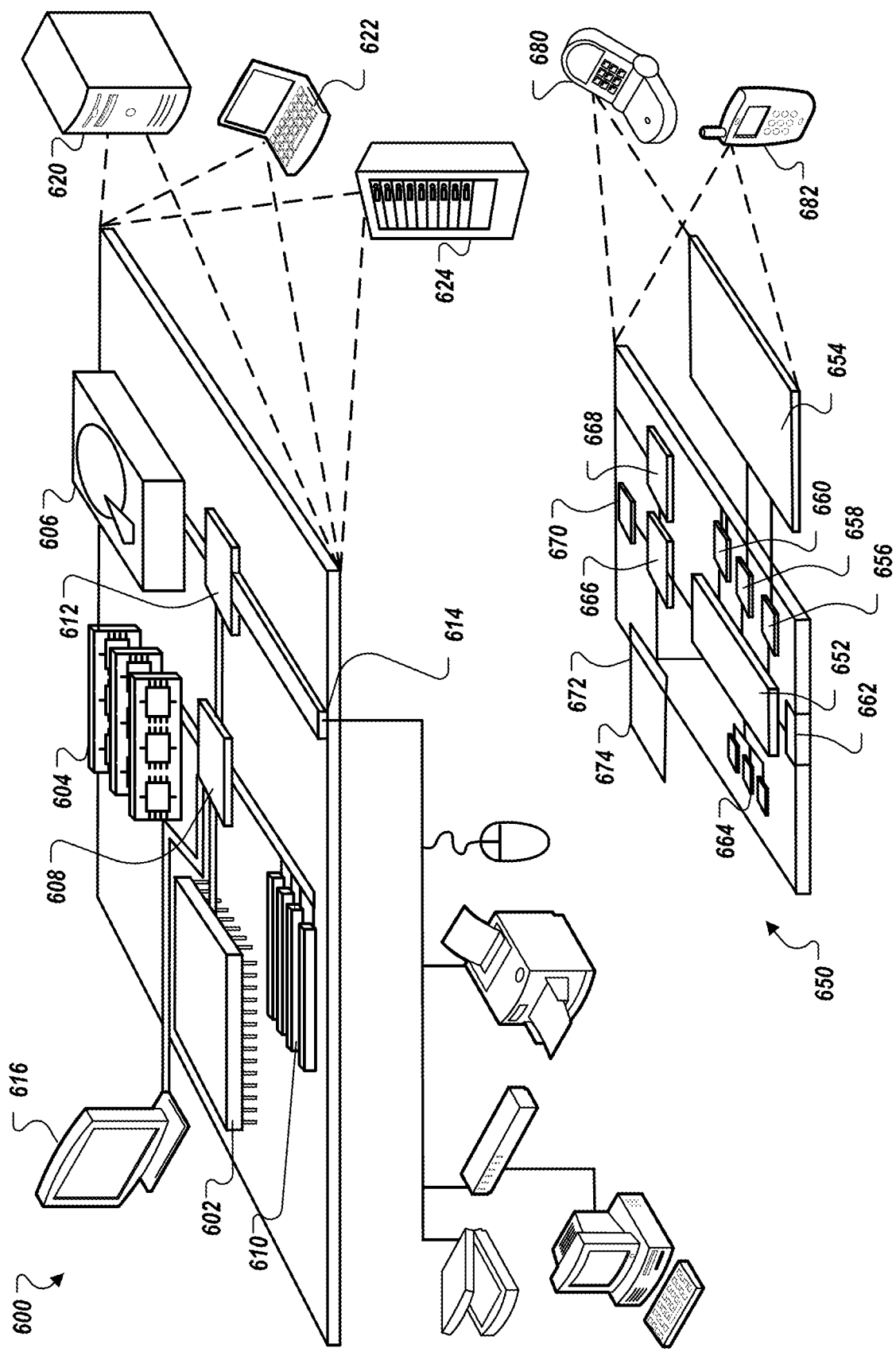
FIG. 6 is a block diagram of system components that can be used to implement the systems of FIG. 1 or FIG. 2.

FIG. 6 is a diagram illustrating an example of a computing system used for hash table generation and selecting a candidate alignment location of a genomic read based on a reference genomic read stored in a hash table. The computing system includes computing device 600 and a mobile computing device 650 that can be used to implement the techniques described herein. For example, one or more components of the system 100 or 200 could be an example of the computing device 600 or the mobile computing device 650, such as the computer 104, devices that access information from the computer 104, or a server that accesses or stores information regarding the operations performed by the computer 104.

The computing device 600 is intended to represent various forms of digital computers, such as laptops, desktops, workstations, personal digital assistants, servers, blade servers, mainframes, and other appropriate computers. The mobile computing device 650 is intended to represent various forms of mobile devices, such as personal digital assistants, cellular telephones, smart-phones, mobile embedded radio systems, radio diagnostic computing devices, and other similar computing devices. The components shown here, their connections and relationships, and their functions, are meant to be examples only, and are not meant to be limiting.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses may be used, as appropriate, along with multiple memories and types of memory. In addition, multiple computing devices may be connected, with each device providing portions of the operations (e.g., as a server bank, a group of blade servers, or a multi-processor system). In some implementations, the processor 602 is a single threaded processor. In some implementations, the processor 602 is a multi-threaded processor. In some implementations, the processor 602 is a quantum computer.

The memory 604 stores information within the computing device 600. In some implementations, the memory 604 is a volatile memory unit or units. In some implementations, the memory 604 is a non-volatile memory unit or units. The memory 604 may also be another form of computer-readable medium, such as a magnetic or optical disk.

The storage device 606 is capable of providing mass storage for the computing device 600. In some implementations, the storage device 606 may be or include a computer-readable medium, such as a floppy disk device, a hard disk device, an optical disk device, or a tape device, a flash memory or other similar solid-state memory device, or an array of devices, including devices in a storage area network or other configurations. Instructions can be stored in an information carrier. The instructions, when executed by one or more processing devices (for example, processor 602), perform one or more methods, such as those described above. The instructions can also be stored by one or more storage devices such as computer- or machine readable mediums (for example, the memory 604, the storage device 606, or memory on the processor 602). The high-speed interface 608 manages bandwidth-intensive operations for the computing device 600, while the low-speed interface 612 manages lower bandwidth-intensive operations. Such allocation of functions is an example only. In some implementations, the high speed interface 608 is coupled to the memory 604, the display 616 (e.g., through a graphics processor or accelerator), and to the high-speed expansion ports 610, which may accept various expansion cards (not shown). In the implementation, the low-speed interface 612 is coupled to the storage device 606 and the low-speed expansion port 614. The low-speed expansion port 614, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. In addition, it may be implemented in a personal computer such as a laptop computer 622. It may also be implemented as part of a rack server system 624. Alternatively, components from the computing device 600 may be combined with other components in a mobile device, such as a mobile computing device 650. Each of such devices may include one or more of the computing device 600 and the mobile computing device 650, and an entire system may be made up of multiple computing devices communicating with each other.

The mobile computing device 650 includes a processor 652, a memory 664, an input/output device such as a display 654, a communication interface 666, and a transceiver 668, among other components. The mobile computing device 650 may also be provided with a storage device, such as a micro-drive or other device, to provide additional storage. Each of the processor 652, the memory 664, the display 654, the communication interface 666, and the transceiver 668, are interconnected using various buses, and several of the components may be mounted on a common motherboard or in other manners as appropriate.

The processor 652 can execute instructions within the mobile computing device 650, including instructions stored in the memory 664. The processor 652 may be implemented as a chipset of chips that include separate and multiple analog and digital processors. The processor 652 may provide, for example, for coordination of the other components of the mobile computing device 650, such as control of user interfaces, applications run by the mobile computing device 650, and wireless communication by the mobile computing device 650.

The processor 652 may communicate with a user through a control interface 658 and a display interface 656 coupled to the display 654. The display 654 may be, for example, a TFT (Thin-Film-Transistor Liquid Crystal Display) display or an OLED (Organic Light Emitting Diode) display, or other appropriate display technology. The display interface 656 may include appropriate circuitry for driving the display 654 to present graphical and other information to a user. The control interface 658 may receive commands from a user and convert them for submission to the processor 652. In addition, an external interface 662 may provide communication with the processor 652, so as to enable near area communication of the mobile computing device 650 with other devices. The external interface 662 may provide, for example, for wired communication in some implementations, or for wireless communication in other implementations, and multiple interfaces may also be used.

The memory 664 stores information within the mobile computing device 650. The memory 664 can be implemented as one or more of a computer-readable medium or media, a volatile memory unit or units, or a non-volatile memory unit or units. An expansion memory 674 may also be provided and connected to the mobile computing device 650 through an expansion interface 672, which may include, for example, a SIMM (Single In Line Memory Module) card interface. The expansion memory 674 may provide extra storage space for the mobile computing device 650, or may also store applications or other information for the mobile computing device 650. Specifically, the expansion memory 674 may include instructions to carry out or supplement the processes described above, and may include secure information also. Thus, for example, the expansion memory 674 may be provide as a security module for the mobile computing device 650, and may be programmed with instructions that permit secure use of the mobile computing device 650. In addition, secure applications may be provided via the SIMM cards, along with additional information, such as placing identifying information on the SIMM card in a non-hackable manner.

The memory may include, for example, flash memory and/or NVRAM memory (nonvolatile random access memory), as discussed below. In some implementations, instructions are stored in an information carrier such that the instructions, when executed by one or more processing devices (for example, processor 652), perform one or more methods, such as those described above. The instructions can also be stored by one or more storage devices, such as one or more computer- or machine-readable mediums (for example, the memory 664, the expansion memory 674, or memory on the processor 652). In some implementations, the instructions can be received in a propagated signal, for example, over the transceiver 668 or the external interface 662.

The mobile computing device 650 may communicate wirelessly through the communication interface 666, which may include digital signal processing circuitry in some cases. The communication interface 666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), LTE, 6G/6G cellular, among others. Such communication may occur, for example, through the transceiver 668 using a radio frequency. In addition, short-range communication may occur, such as using a Bluetooth, Wi-Fi, or other such transceiver (not shown). In addition, a GPS (Global Positioning System) receiver module 670 may provide additional navigation- and location-related wireless data to the mobile computing device 650, which may be used as appropriate by applications running on the mobile computing device 650.

The mobile computing device 650 may also communicate audibly using an audio codec 660, which may receive spoken information from a user and convert it to usable digital information. The audio codec 660 may likewise generate audible sound for a user, such as through a speaker, e.g., in a handset of the mobile computing device 650. Such sound may include sound from voice telephone calls, may include recorded sound (e.g., voice messages, music files, among others) and may also include sound generated by applications operating on the mobile computing device 650.

The mobile computing device 650 may be implemented in a number of different forms, as shown in the figure. For example, it may be implemented as a cellular telephone 680. It may also be implemented as part of a smart-phone 682, personal digital assistant, or other similar mobile device.

A number of implementations have been described. Nevertheless, it will be understood that various modifications may be made without departing from the spirit and scope of the disclosure. For example, various forms of the flows shown above may be used, with steps re-ordered, added, or removed.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

What is claimed is:

1. A method for software accelerated genomic data read mapping a genomic data read to a reference genome, the method comprising:
   (a) obtaining, by one or more computers, a first k-mer seed from the genomic data read;
   (b) generating, by the one or more computers, a hash value representing a genomic signature by applying a hash function to the first k-mer seed;
   (c) determining, by the one or more computers, a reference sequence location that matches at least a portion of the first k-mer seed using a hash data structure, wherein the hash data structure comprises N data cells and wherein a first data cell of the N data cells includes (i) a first portion storing a predetermined genomic signature derived from the portion of the first k-mer seed and (ii) a second portion storing a value that corresponds to a location within the reference genome that matches at least the portion of the first k-mer seed;

(d) determining, by the one or more computers, a number of mismatches for the first k-mer seed based on comparing genomic data of the genomic data read to genomic data of the reference genome;

(e) determining, by the one or more computers, whether the number of mismatches satisfies a threshold number of mismatches;

continuing to perform operations corresponding to (a)-(e) for an additional k-mer seed at each iteration, wherein the additional k-mer seed corresponds to a portion of the genomic data read different than the first k-mer seed, until a determination is made that the number of mismatches for a last additional k-mer seed satisfies a second mismatch threshold;

determining that the number of mismatches for the last additional k-mer seed satisfies the second mismatch threshold;

based on a determination that the number of mismatches satisfies the second mismatch threshold, terminating the continued performance of the operations corresponding to (a)-(e) prior to a subsequent pass; and selecting an actual alignment for the genomic data read based on the last additional k-mer seed.

2. The method of claim 1, wherein obtaining the first k-mer seed from the genomic data read comprises:

obtaining a first k bases of the genomic data read as the first k-mer seed.

3. The method of claim 1, comprising obtaining a set of k-mer seeds, that include the additional k-mer seed from the genomic data read, wherein selecting the actual alignment for the genomic data read comprises:

generating second genomic signatures for the set of k-mer seeds; and selecting a subset of the set of k-mer seeds based on the second genomic signatures.

4. The method of claim 3, wherein selecting the subset of the set of k-mer seeds based on the second genomic signatures comprises:

performing one or more modulo operations including a modulo operation on each genomic signature of the second genomic signatures; and selecting the subset of the set of k-mer seeds based on results of the one or more modulo operations and a predetermined criterion.

5. The method of claim 1, wherein continuing to perform the operations corresponding to (a)-(e) comprises:

determining, by the one or more computers, a reference sequence location for each k-mer seed of a set of k-mer seeds, that include the additional k-mer seed, that matches at least a portion of a given k-mer seed using the hash data structure; and generating a candidate location list including a reference sequence location for each k-mer seed of the set of k-mer seeds.

6. The method of claim 5, comprising:

sorting the reference sequence locations of the candidate location list according to a number of k-mer seeds paired with the given reference sequence location in the hash data structure; and determining a number of mismatches for each of the reference sequence locations of the sorted candidate location list compared to the reference genome in an order of the sorted candidate location list.

7. The method of claim 6, comprising:

determining a number of mismatches for a first candidate location of the reference sequence locations of the sorted candidate location list satisfies the second mismatch threshold; and selecting the first candidate location as the actual alignment.

8. The method of claim 7, wherein the second mismatch threshold is different than the threshold number of mismatches.

9. The method of claim 1, comprising:

generating second genomic signatures for each k-mer seed of an obtained set of k-mer seeds including the additional k-mer seed;

performing second one or more modulo operations including a modulo operation on each genomic signature of the second genomic signatures; and selecting a subset of the set of k-mer seeds based on results of the second one or more modulo operations and a predetermined criterion.

10. The method of claim 9, comprising:

determining a reference sequence location for each k-mer seed of the subset that matches at least a portion of a given k-mer seed using the hash data structure; and generating a second candidate location list including a reference sequence location for each k-mer seed of the subset.

11. The method of claim 10, comprising:

sorting the reference sequence locations of the second candidate location list according to a number of k-mer seeds paired with the given reference sequence location in the hash data structure; and determining a number of mismatches for each of the reference sequence locations of the sorted second candidate location list compared to the reference genome in an order of the sorted second candidate location list.

12. The method of claim 11, comprising:

determining a number of mismatches for a second candidate location of the reference sequence locations of the sorted candidate location list satisfies the second mismatch threshold; and selecting the first candidate location as the actual alignment.

13. The method of claim 1, wherein obtaining the first k-mer seed from the genomic data read comprises:

obtaining a set of k-mer seeds from the genomic data read, the method comprising:

filtering the set of k-mer seeds by performing a first filtering process and a second filtering process different than the first filtering process, wherein the first filtering process comprises generating hash values for each of the set of k-mer seeds by applying a first hash function to each respective k-mer seed, wherein the hash data structure is generated from a second filtered set of k-mers, wherein the second filtered set of k-mers are generated using the first filtering process and the second filtering process on a second set of k-mers extracted from the reference genome.

14. A non-transitory computer-readable medium storing one or more instructions executable by a computer system to perform operations for software accelerated genomic data read mapping a genomic data read to a reference genome, the operations comprising:

(a) obtaining, by one or more computers, a first k-mer seed from the genomic data read;

(b) generating, by the one or more computers, a hash value representing a genomic signature by applying a hash function to the first k-mer seed;

(c) determining, by the one or more computers, a reference sequence location that matches at least a portion of the first k-mer seed using a hash data structure, wherein the hash data structure comprises N data cells and wherein a first data cell of the N data cells includes (i) a first portion storing a predetermined genomic signature derived from the portion of the first k-Rizk-mer seed and (ii) a second portion storing a value that corresponds to a location within the reference genome that matches at least the portion of the first k-mer seed;

(d) determining, by the one or more computers, a number of mismatches for the first k-mer seed based on comparing genomic data of the genomic data read to genomic data of the reference genome;

(e) determining, by the one or more computers, whether the number of mismatches satisfies a threshold number of mismatches;

continuing to perform operations corresponding to (a)-(e) for an additional k-mer seed at each iteration, wherein the additional k-mer seed corresponds to a portion of the genomic data read different than the first k-mer seed, until a determination is made that the number of mismatches for a last additional k-mer seed satisfies a second mismatch threshold;

determining that the number of mismatches for the last additional k-mer seed satisfies the second mismatch threshold;

based on a determination that the number of mismatches satisfies the second mismatch threshold, terminating the continued performance of the operations corresponding to (a)-(e) prior to a subsequent pass; and selecting an actual alignment for the genomic data read based on the last additional k-mer seed.

15. The medium of claim 14, wherein obtaining the first k-mer seed from the genomic data read comprises:

obtaining a first k bases of the genomic data read as the first k-mer seed.

16. The medium of claim 14, comprising obtaining a set of k-mer seeds, that include the additional k-mer seed from the genomic data read, wherein selecting the actual alignment for the genomic data read comprises:

generating second genomic signatures for the set of k-mer seeds; and selecting a subset of the set of k-mer seeds based on the second genomic signatures.

17. The medium of claim 16, wherein selecting the subset of the set of k-mer seeds based on the second genomic signatures comprises:

performing one or more modulo operations including a modulo operation on each genomic signature of the second genomic signatures; and selecting the subset of the set of k-mer seeds based on results of the one or more modulo operations and a predetermined criterion.

18. The medium of claim 14, wherein continuing to perform the operations corresponding to (a)-(e) comprises:

determining, by the one or more computers, a reference sequence location for each k-mer seed of a set of k-mer seeds, that include the additional k-mer seed, that matches at least a portion of a given k-mer seed using the hash data structure; and generating a candidate location list including a reference sequence location for each k-mer seed of the set of k-mer seeds.

19. A system comprising:

one or more processors; and machine-readable media interoperably coupled with the one or more processors and storing one or more instructions that, when executed by the one or more processors, perform operations for software accelerated genomic data read mapping a genomic data read to a reference genome, the operations comprising:

(a) obtaining, by one or more computers, a first k-mer seed from the genomic data read;

(b) generating, by the one or more computers, a hash value representing a genomic signature by applying a hash function to the first k-mer seed;

(c) determining, by the one or more computers, a reference sequence location that matches at least a portion of the first k-mer seed using a hash data structure, wherein the hash data structure comprises N data cells and wherein a first data cell of the N data cells includes (i) a first portion storing a predetermined genomic signature derived from the portion of the first k-mer seed and (ii) a second portion storing a value that corresponds to a location within the reference genome that matches at least the portion of the first k-mer seed;

(d) determining, by the one or more computers, a number of mismatches for the first k-mer seed based on comparing genomic data of the genomic data read to genomic data of the reference genome;

(e) determining, by the one or more computers, whether the number of mismatches satisfies a threshold number of mismatches;

continuing to perform operations corresponding to (a)-(e) for an additional k-mer seed at each iteration, wherein the additional k-mer seed corresponds to a portion of the genomic data read different than the first k-mer seed, until a determination is made that the number of mismatches for a last additional k-mer seed satisfies a second mismatch threshold;

determining that the number of mismatches for the last additional k-mer seed satisfies the second mismatch threshold;

based on a determination that the number of mismatches satisfies the second mismatch threshold, terminating the continued performance of the operations corresponding to (a)-(e) prior to a subsequent pass; and selecting an actual alignment for the genomic data read based on the last additional k-mer seed.

20. The system of claim 19, wherein obtaining the first k-mer seed from the genomic data read comprises:

obtaining a first k bases of the genomic data read as the first k-mer seed.

* * * * *